(12) United States Patent  
Samuel et al.

(10) Patent No.: US 8,480,712 B1
(45) Date of Patent: Jul. 9, 2013

(54) SYSTEM AND METHOD FOR PERFORMING SPINAL FIXATION

(75) Inventors: Forrest Samuel, San Diego, CA (US); Rob German, Carlsbad, CA (US); Rich Mueller, Carlsbad, CA (US); Eric Dasso, Encinitas, CA (US); Robert Riley, Del Mar, CA (US); Dan Ahlgren, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 742 days.

(21) Appl. No.: 12/535,671

(22) Filed: Aug. 4, 2009

Related U.S. Application Data

(63) Continuation-in-part of application No. 11/031,506, filed on Jan. 6, 2005, now Pat. No. 7,833,251.

(60) Provisional application No. 60/534,650, filed on Jan. 6, 2004.

(51) Int. Cl.
*A61B 17/70* (2006.01)

(52) U.S. Cl.
USPC .......................................................... 606/250

(58) Field of Classification Search
USPC ................................................. 606/250–279
See application file for complete search history.

(56) References Cited

U.S. PATENT DOCUMENTS

| 4,998,936 | A | 3/1991 | Mehdian |
| 5,084,049 | A | 1/1992 | Asher et al. |
| 5,154,718 | A | 10/1992 | Cozad et al. |
| 5,505,731 | A * | 4/1996 | Tornier .......................... 606/261 |
| 5,545,163 | A * | 8/1996 | Miller et al. ................... 606/287 |
| 5,569,246 | A | 10/1996 | Ojima et al. |
| 5,624,442 | A | 4/1997 | Mellinger et al. |
| 5,669,910 | A | 9/1997 | Korhonen et al. |
| 5,688,272 | A | 11/1997 | Montague et al. |
| 5,947,966 | A | 9/1999 | Drewry et al. |
| 5,980,521 | A | 11/1999 | Montague et al. |
| 5,980,523 | A | 11/1999 | Jackson et al. |
| 6,083,226 | A * | 7/2000 | Fiz ................................. 606/252 |
| 6,113,600 | A | 9/2000 | Drummond et al. |
| 6,136,003 | A | 10/2000 | Hoeck et al. |
| 6,139,548 | A | 10/2000 | Errico |
| 6,171,311 | B1 | 1/2001 | Richelsoph |
| 6,179,838 | B1 | 1/2001 | Fiz |
| 6,217,578 | B1 | 4/2001 | Crozet et al. |
| 6,234,705 | B1 | 5/2001 | Troxell |
| 6,238,396 | B1 | 5/2001 | Lombardo |
| 6,283,967 | B1 | 9/2001 | Troxell et al. |
| 6,306,137 | B2 | 10/2001 | Troxell |
| 6,328,740 | B1 | 12/2001 | Richelsoph |
| 6,328,741 | B1 | 12/2001 | Richelsoph |
| 6,402,751 | B1 | 6/2002 | Hoeck et al. |

(Continued)

FOREIGN PATENT DOCUMENTS

| EP | 0746255 | 11/2002 |
| EP | 1743585 | 1/2007 |
| WO | 2006/025919 | 3/2006 |

*Primary Examiner* — Eduardo C Robert
*Assistant Examiner* — Tara Carter
(74) *Attorney, Agent, or Firm* — Jonathan Spangler; Rory Schermerhorn

(57) ABSTRACT

A spinal fixation system suitable for effecting fixation between adjacent vertebral levels within the spine. The spinal fixation system of the present invention includes a pair single axis or "fixed" pedicle screw assemblies, a pair of poly-axial pedicle screw assemblies, a pair of cannulated rod members, and a transverse connector spanning between the pair of cannulated rod members.

17 Claims, 23 Drawing Sheets

U.S. PATENT DOCUMENTS

| | | |
|---|---|---|
| 6,413,258 B1 | 7/2002 | Bernhardt, Jr. |
| 6,485,491 B1 | 11/2002 | Farris et al. |
| 6,524,310 B1 | 2/2003 | Lombardo et al. |
| 6,554,832 B2 | 4/2003 | Shluzas |
| 6,602,253 B2 | 8/2003 | Richelsoph et al. |
| 6,616,668 B2 | 9/2003 | Altarac et al. |
| 6,736,817 B2 | 5/2004 | Troxell et al. |
| 6,752,807 B2 | 6/2004 | Lin et al. |
| 6,761,721 B2 | 7/2004 | Burgess et al. |
| 6,783,526 B1 | 8/2004 | Lin et al. |
| 6,872,208 B1 | 3/2005 | McBride et al. |
| 6,875,211 B2 | 4/2005 | Nichols et al. |
| 6,887,241 B1 | 5/2005 | McBride et al. |
| 6,958,066 B2 | 10/2005 | Richelsoph et al. |
| 6,960,212 B2 | 11/2005 | Richelsoph et al. |
| 7,029,474 B2 | 4/2006 | Richelsoph et al. |
| 7,066,938 B2 | 6/2006 | Slivka et al. |
| 7,083,622 B2 | 8/2006 | Simonson |
| 7,104,993 B2 | 9/2006 | Baynham et al. |
| 7,122,036 B2 | 10/2006 | Vanacker |
| 7,137,986 B2 | 11/2006 | Troxell et al. |
| 7,160,301 B2 | 1/2007 | Cordaro |
| 7,406,775 B2 | 8/2008 | Funk et al. |
| 2002/0052603 A1 | 5/2002 | Nichols et al. |
| 2002/0143330 A1 | 10/2002 | Shluzas |
| 2002/0169448 A1 | 11/2002 | Vanacker |
| 2003/0023244 A1 | 1/2003 | Richelsoph et al. |
| 2003/0153917 A1 | 8/2003 | Richelsoph et al. |
| 2004/0116928 A1 | 6/2004 | Young et al. |
| 2005/0090821 A1 | 4/2005 | Berrevoets et al. |
| 2006/0058789 A1 | 3/2006 | Kim et al. |
| 2006/0064091 A1 | 3/2006 | Ludwig et al. |
| 2006/0064093 A1 | 3/2006 | Thramann et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2007/0173829 A1 | 7/2007 | Drewry et al. |
| 2007/0213721 A1 | 9/2007 | Markworth et al. |
| 2007/0213723 A1 | 9/2007 | Markworth et al. |
| 2007/0233090 A1 | 10/2007 | Naifeh |
| 2007/0270808 A1 | 11/2007 | Drewry et al. |
| 2007/0270809 A1 | 11/2007 | Drewry et al. |
| 2007/0288009 A1 | 12/2007 | Brown et al. |
| 2008/0109039 A1 | 5/2008 | Michielli et al. |
| 2008/0172093 A1 | 7/2008 | Nilsson |
| 2008/0177315 A1 | 7/2008 | Usher |

\* cited by examiner

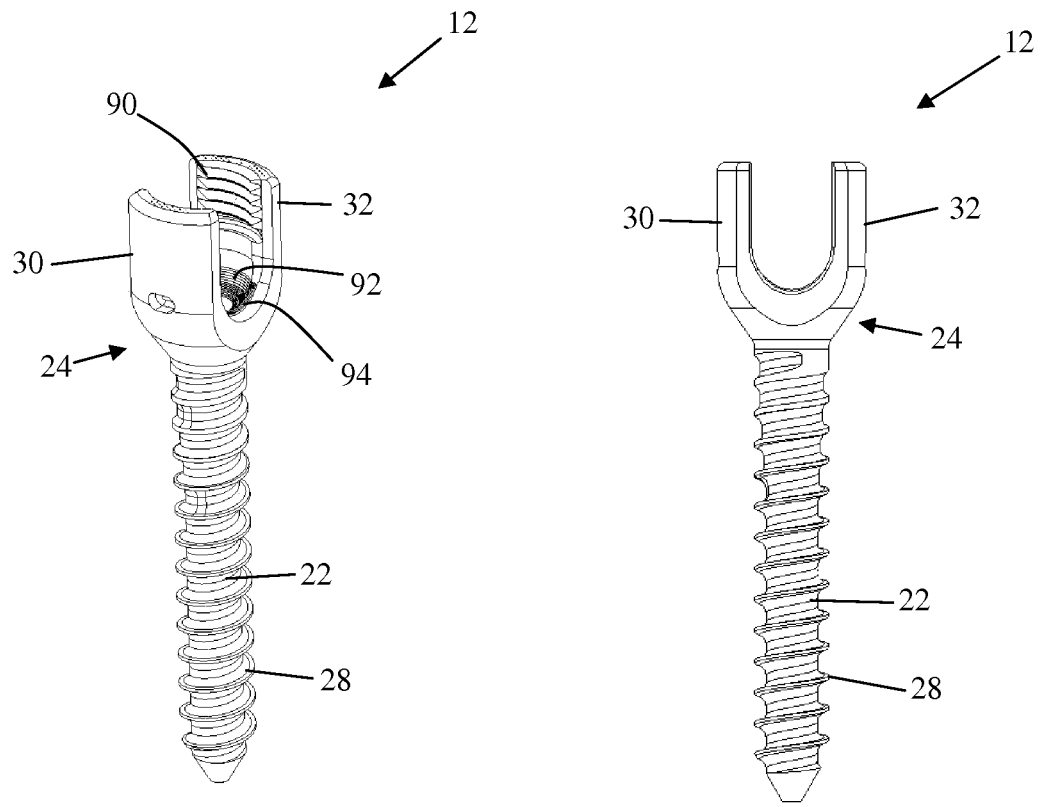
Fig. 10                    Fig. 11
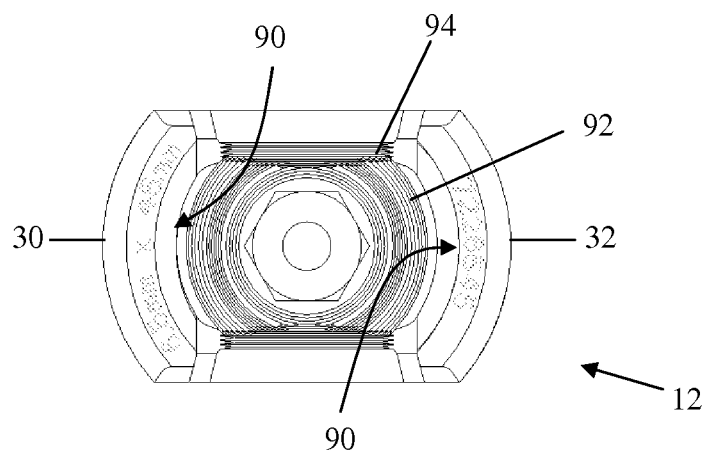
Fig. 12

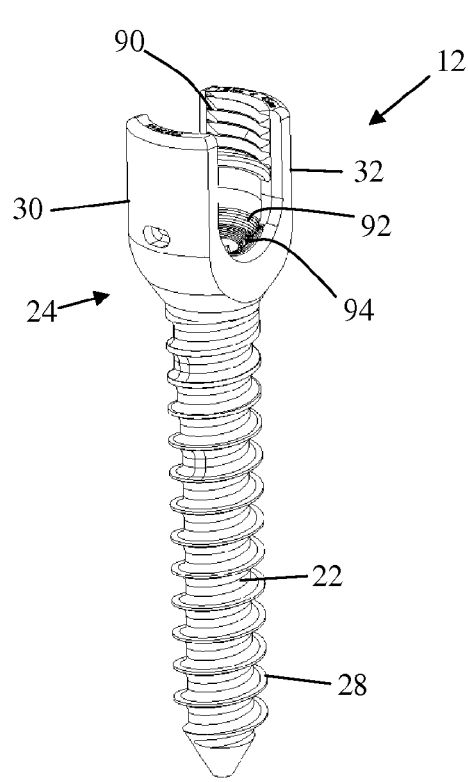
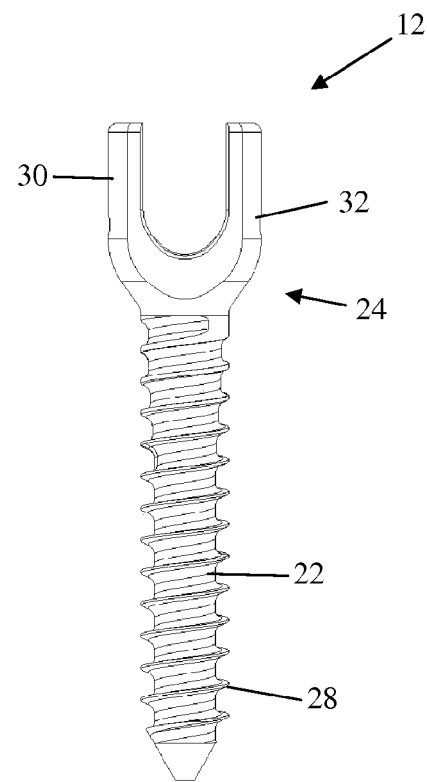
Fig. 13
Fig. 14
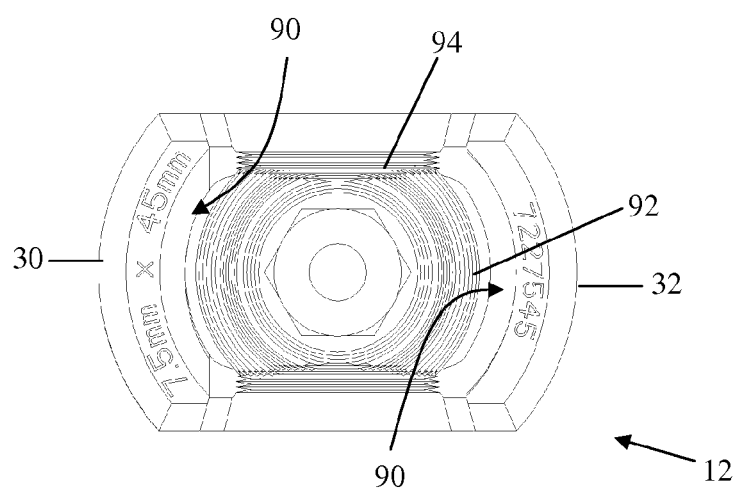
Fig. 15

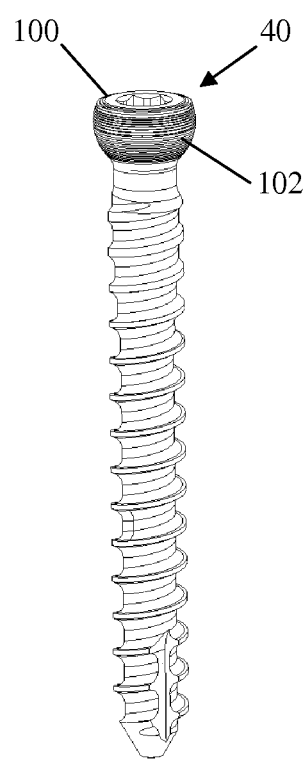
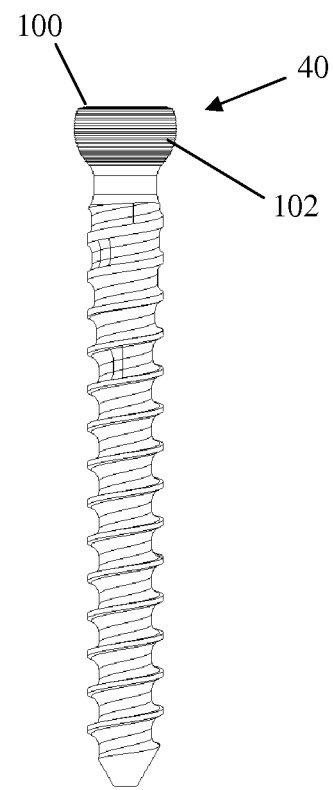
Fig. 17  Fig. 18
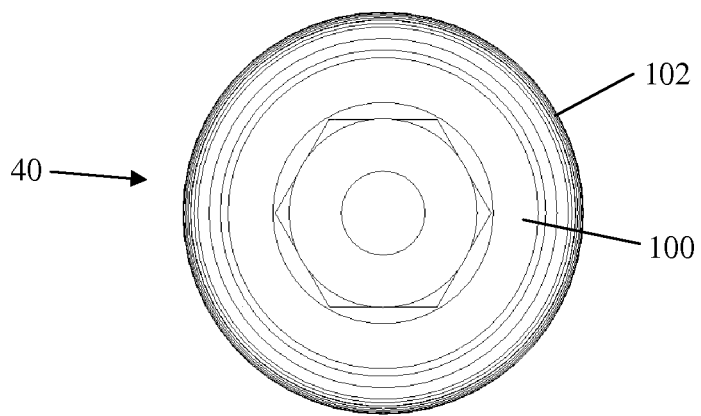
Fig. 19

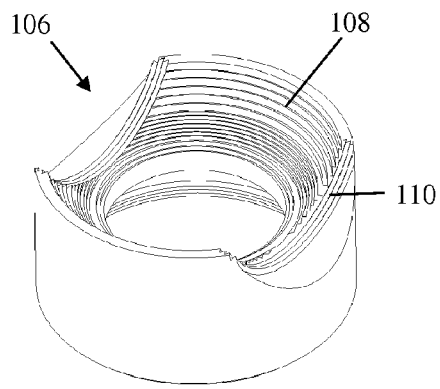 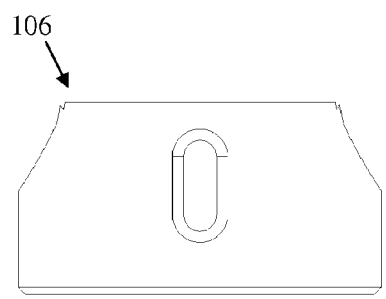
Fig. 23	Fig. 24
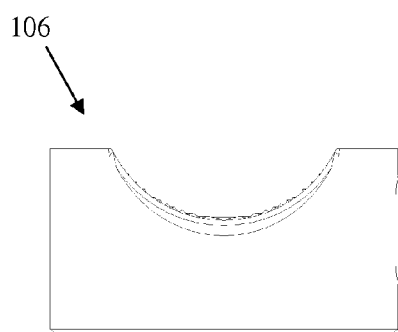 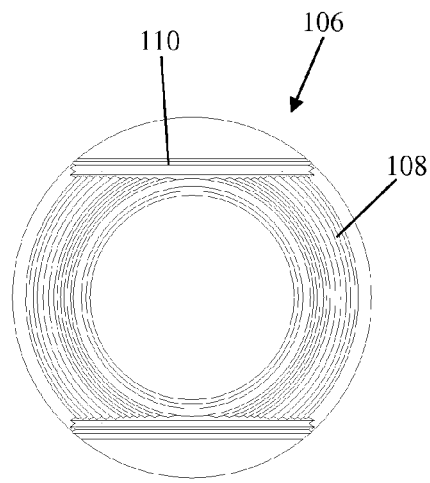
Fig. 25	Fig. 26

SYSTEM AND METHOD FOR PERFORMING SPINAL FIXATION

CROSS-REFERENCES TO RELATED APPLICATIONS

The present application is a continuation-in-part of U.S. application Ser. No. 11/031,506, filed Jan. 6, 2005 now U.S. Pat. No. 7,833,251 and entitled "System and Methods for Performing Spinal Fixation," which claims priority to U.S. Provisional Application No. 60/534,650, filed Jan. 6, 2004 and entitled "System and Methods for Performing Spinal Fixation," the complete disclosures of which are incorporated by reference in their entireties as if set forth fully herein. The present application also claims priority under 35 U.S.C. §119 (e) to U.S. Provisional Application No. 61/086,125, filed Aug. 4, 2008 and entitled "System and Methods for Performing Spinal Fixation," the complete disclosure of which is hereby incorporated by reference.

BACKGROUND OF THE INVENTION

I. Field of the Invention

The present invention relates to medical devices and methods generally aimed at spinal surgery. In particular, the disclosed system and associated methods relate to performing spinal fixation.

II. Discussion of the Prior Art

Fixation systems are often surgically implanted into a patient to aid in the stabilization of a damaged spine or to aid in the correction of other spinal geometric deformities. Spinal fixation systems are often constructed as a framework stabilizing a particular section of the spine. Existing systems often use a combination of rods, plates, pedicle screws and bone hooks for fixing the framework to the affected vertebrae. The configuration required for each patient varies due to the patient's specific anatomical characteristics and ailments. As a result, there is a need for a modular spinal fixation system that allows for a large degree of custom configurations.

The present invention is directed at addressing this need and eliminating, or at least reducing, the effects of the shortcomings of the prior art systems as described above.

SUMMARY OF THE INVENTION

The present invention discloses a system and methods for performing spinal fixation. The system includes at least one pair of elongate members, a plurality of pedicle screws and at least one transverse connector.

The elongate members are installed along the length of the spine of the patient. The elongate members are coupled to vertebrae by a set of pedicle screws. In addition, to increase the rigidity of the fixation system, at least one transverse connector may be used to interconnect the elongate members.

The elongate members may include rods with sufficient length to span the affected area. The rods are constructed with an outer surface that is compatible with the head of a pedicle screw, bone hook or transverse connector. The elongate member may be of a length sufficient to span the entire length of the affected spinal section. Alternatively, the elongate members may be constructed from a plurality of the members coupled together.

Pedicle screws are included to couple the elongate rod members to the bony structures in the spine. Pedicle screws may have heads that are rigid with respect to the screw shank or heads that may be angularly adjusted with respect to the screw shank. As used herein, a poly-axial pedicle screw shall be understood to encompass the latter configuration.

The transverse connectors are designed to extend between and couple a pair of elongate members. The transverse connectors are adjustable in length along the longitudinal axis and both ends are able to rotate along the longitudinal axis. Furthermore, the angle of each end with respect to the longitudinal axis is adjustable.

BRIEF DESCRIPTION OF THE DRAWINGS

Other objects and advantages of the invention will become apparent upon reading the following detailed description and upon reference to the drawings in which:

FIGS. 10-12 are perspective, side and top views, respectively, of a fixed angle pedicle screw assembly of the present invention, having a shaft diameter of 6.5 mm and a length of 45 mm;

FIGS. 13-15 are perspective, side and top views, respectively, of a fixed angle pedicle screw assembly of the present invention, having a shaft diameter of 7.5 mm and a length of 45 mm;

FIGS. 17-19 are perspective, side and top views, respectively, of a screw member forming part of the poly-axial pedicle screw system of the present invention;

FIGS. 23-26 are perspective, first side, second side, and top views, respectively, of a load ring forming part of the poly-axial pedicle screw system of the present invention.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and method for performing spinal fixation disclosed herein boast a variety of inventive features and components that warrant patent protection, both individually and in combination.

Figure 1:
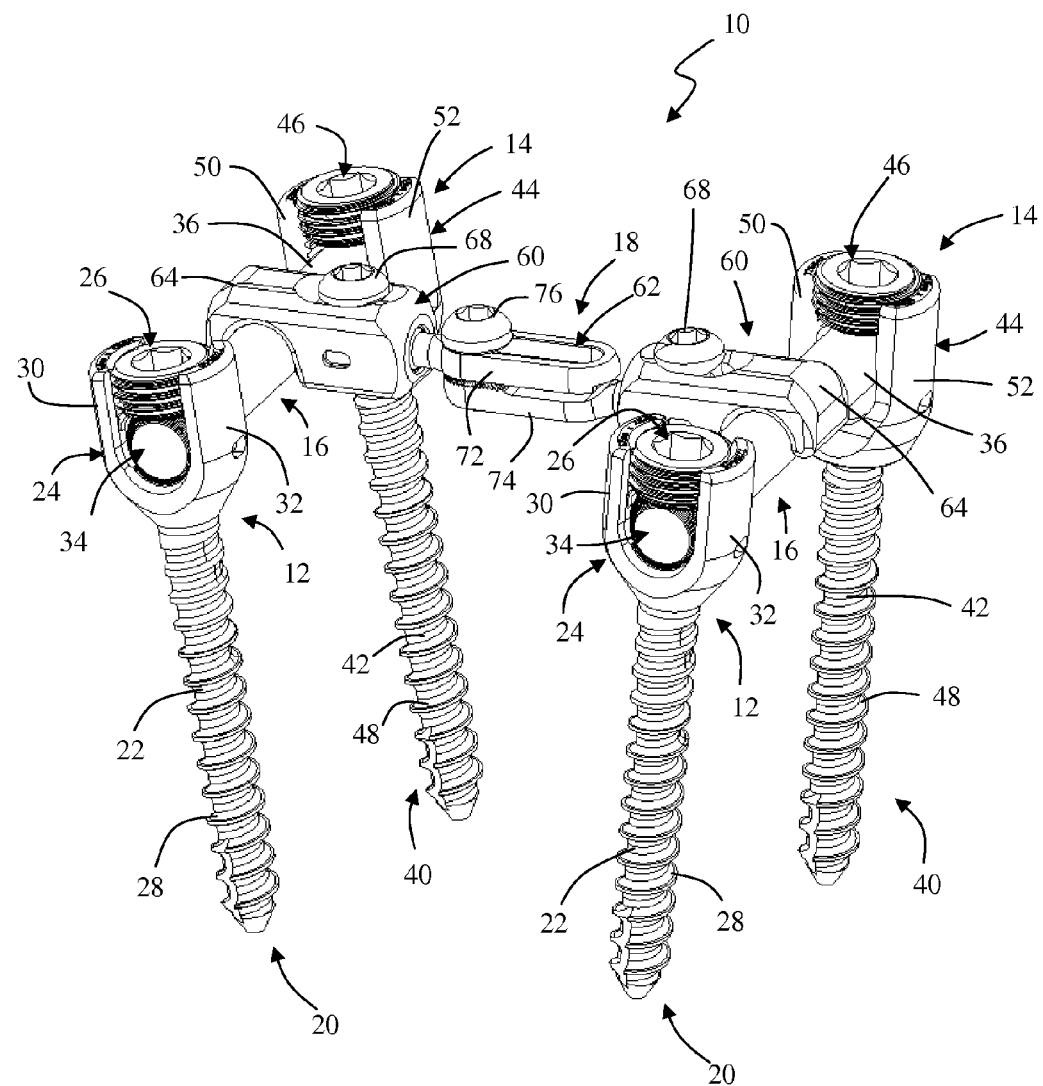
FIG. 1 is a perspective view of a spinal fixation system of the present invention incorporating (by way of example only) a single axis pedicle screw, a poly-axial pedicle screw, a spherical-ended rod member, and a transverse connector, each forming a unique and patentable aspect of the present invention.

FIG. 1 is a perspective view of a spinal fixation system 10 of the present invention. The spinal fixation system 10 is suitable for effecting fixation between adjacent vertebral levels within the spine. The spinal fixation system 10 of the present invention as shown in this embodiment includes a pair single axis or "fixed" pedicle screw assemblies 12, a pair of poly-axial pedicle screw assemblies 14, a pair of cannulated rod members 16, and a transverse connector 18 spanning between the pair of cannulated rod members 16. Each of the single axis pedicle screw assembly 12, poly-axial pedicle screw assembly 14, cannulated rod member 16, and transverse connector 18 form a unique and patentable aspect of the present invention.

The spinal fixation system 10 is shown and described herein as a "single level" fixation system, meaning the single axis pedicle screw assemblies 12 will be fixed to a first vertebral body, the poly-axial pedicle screw assemblies 14 will be fixed to a second vertebral body (adjacent to the first vertebral body), the rod members 16 will be disposed on either side of (and generally parallel to) the midline of the spine, and the transverse connector 18 will span between the rod members 16 generally perpendicularly to the mid-line of the spine. Although shown and described herein as a "single level" construct, it will be appreciated that the spinal fixation system 10 of the present invention may be used in multi-level procedures without departing from the scope of the present invention.

Moreover, before addressing the specifics of each the single axis pedicle screw assembly 12, poly-axial pedicle screw assembly 14, cannulated rod member 16, and transverse connector 18, it is to be appreciated that the combination shown in FIG. 1 is set forth by way of example only. That is, the spinal fixation system 10 of the present invention may comprise any number of variations of that shown without departing from the scope of the invention. For example, the spinal fixation system 10 may comprise four (4) of the single axis pedicle screw assemblies 12, four (4) of the poly-axial pedicle screw assemblies 14, and/or any combination of single and poly-axial pedicle screw assemblies 12, 14, in conjunction with the rod members 16 to effect spinal fixation.

Each single axis pedicle screw assembly 12 of the present invention includes a screw member 20 having a shaft 22 and a housing 24, as well as a locking screw 26. The shaft 22 and housing 24 are integrally formed as a unitary article such that the shaft 22 and housing 24 are in fixed relation, hence the term "single axis" to describe this type of pedicle screw assembly 12 according to the present invention. The shaft 22 includes a thread 28 suitable for introduction into and purchase within bone. Each housing 24 includes first and second branches 30, 32, which collectively form a generally "U" shaped area dimensioned to receive at least one of a ball portion 34 and/or a rod portion 36 (forming either end of the rod member 16 according to a further aspect of the present invention) and thereafter the locking screw 26. In a preferred aspect, each component of the fixed angle pedicle screw assembly 12 is cannulated (i.e. it is equipped with a longitudinal lumen extends through the locking screw 26 and screw member 20) such that a K-wire may be used to guide the fixed angle pedicle screw assembly 12 into the patient.

Each poly-axial pedicle screw assembly 14 of the present invention includes a screw member 40, a housing 44, and a locking screw 46. The screw member 40 includes a shaft 42. The screw member 40 and housing 44 are separate articles such that the angle of the housing 44 relative to the screw member 40 may be varied in any number of fashions prior to locking them together, hence the term "poly axial" to describe this type of pedicle screw assembly 14 according to the present invention. The shaft 42 includes a thread 48 suitable for introduction into and purchase within bone. Each housing 44 includes first and second branches 50, 52, which collectively form a generally "U" shaped area dimensioned to receive at least one of the ball portion 34 and/or rod portion 36 (forming either end of the rod member 16 according to a further aspect of the present invention) and thereafter the locking screw 46. In a preferred aspect, each component of the poly-axial pedicle screw assembly 14 is cannulated (i.e. it is equipped with a longitudinal lumen extends through the locking screw 46 and screw member 40) such that a K-wire may be used to guide the poly-axial pedicle screw assembly 14 into the patient.

The transverse connector 18 of the present invention includes a pair of rod clamping assemblies 60 capable of fixedly engaging regions on the respective rod members 16, as well as a linkage assembly 62 extending between the rod clamping assemblies 60. Each rod clamping assembly 60 includes a top clamp member 64, a bottom clamp member 66 (not shown), a clamp screw 68, and a poly-axial pivot ring 70 (not shown). The linkage assembly 62 includes a slotted link member 72, a grooved link member 74, and a link screw 76. The operation and details of the rod clamping and linkage assemblies 60, 62 will be described in greater detail below.

Figure 2:
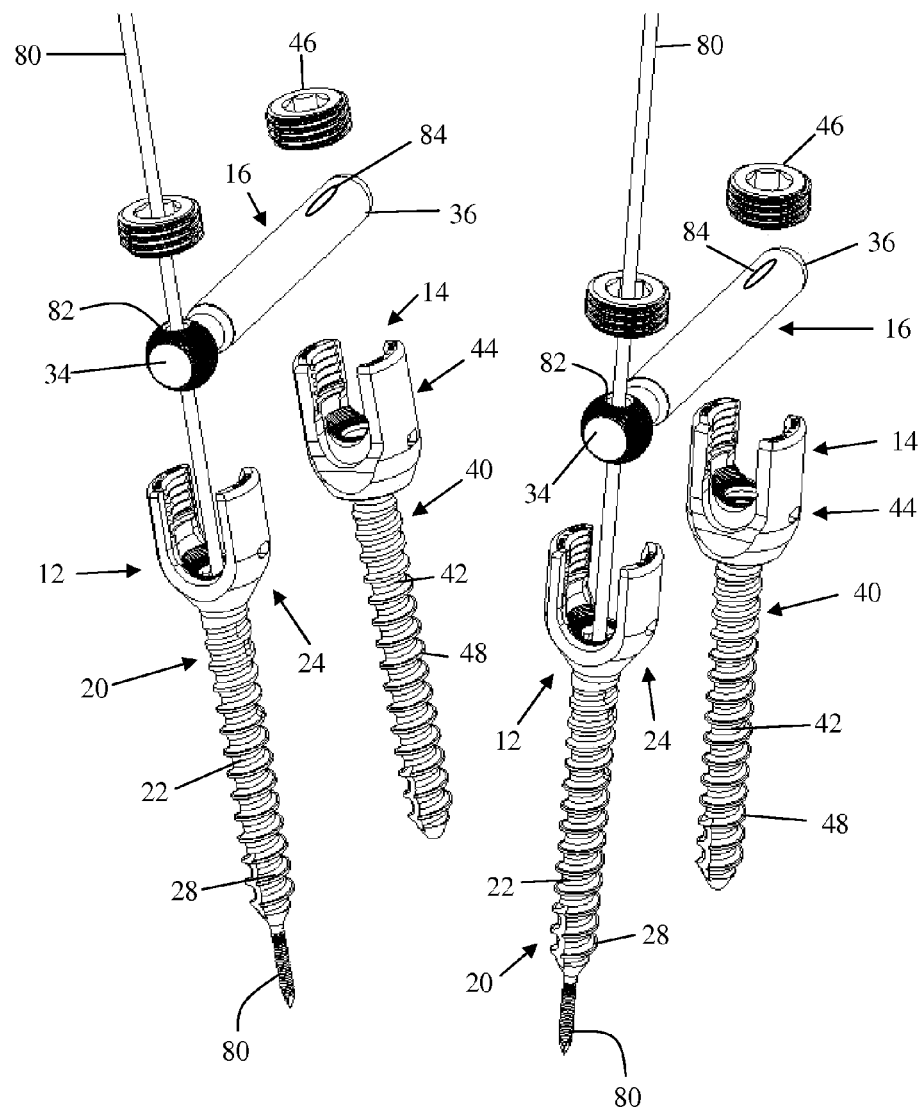
FIG. 2 is a perspective and exploded view of the spinal fixation system shown in FIG. 1 (sans transverse connector) illustrating the method of implanting the pedicle screws and rod member according to the present invention.

FIG. 2 illustrates a method of using the spinal fixation system 10 according to one embodiment of the present invention. As noted above, the fixed and poly-axial pedicle screw assemblies 12, 14 are preferably cannulated (i.e. a longitudinal lumen extends through the locking screws 26, 46 and screw members 20, 40, respectively). As such, each the pedicle screw assemblies 12, 14 of the present invention may be advanced over a K-wire 80 and thereby guided into the patient. More specifically, the K-wires 80 may be used (with or without image guidance, such as X-ray and/or fluoroscopy systems) to target the location and trajectory to introduce the shafts 22, 42 of the screw members 20, 40, respectively, into the pedicle of interest. Once the desired location and trajectory are identified, the screw members 20, 40 may be advanced over a respective K-wire 80 until the distal end of the shafts 22, 42 contact the pedicle, after which point the screw members 20, 40 may be rotated about the K-wire 80 (e.g., by rotating the housings 24, 44 via any suitable instrumentation) until the shafts 22, 42 are introduced a desired depth into the pedicle and/or vertebral body. This may be preceded by any number of suitable preparatory steps, such as drilling and/or tapping a pilot hole to better accommodate the shafts 22, 42 and/or threads 28, 48 prior to the introduction of screw members 20, 40.

Once the screw members 20, 40 have been introduced as described above, rod members 16 may thereafter be advanced into the patient for engagement with the pedicle screw assemblies 12, 14 of the present invention. To facilitate this, the rod member 16 may be provided with one or more cannulations (e.g. cannulation 82 in the ball portion 34 and/or cannulation 84 in the rod region 36) such that one or more ends of the rod member 16 may be guided over a K-wire 80 and into a respective housing 24, 44. Although described herein with the ball portion 34 engaging within the housing 24 of the fixed angle pedicle screw assemblies 12 and the rod portion 36 engaging within the housing 44 of the poly-axial pedicle screw assembly 14, it will be appreciated that this may be reversed in one or both sides without departing from the scope of the present invention. Any number of suitable instruments may be employed to facilitate the above-identified step, including but not limited to a pushing or holding device for guiding the rod member 16 into the patient.

After the rod member 16 is introduced as described above, the locking screws 26, 46 may thereafter be introduced and engaged with the housings 24, 44. It may be desirable to adjust the position of the rod member 16 relative to the pedicle screw assemblies 12, 14 according to a still further aspect of the present invention. More specifically, as will be discussed in greater detail below, the spherical nature of the ball region 34 of the rod member 16 will (prior to locking) allow it to rotate within the housing 24. As such, the ball region 34 will be loosely disposed within the housing 24 such that the remainder of the rod member 16 may be angled therefrom in any number of desired manners (e.g. up, down, side-to-side and/or any variation thereof) depending upon the situation and need. This may advantageously facilitate positioning the rod region 36 into the housing 44 after the ball region 34 has already been positioned within housing 24. Moreover, this may reduce if not eliminate the need to bend the rod member 16 as with traditional rod members of prior art pedicle screw systems.

It may be preferred to distract the screw members 20, 40 prior to fully locking the locking screws 26, 46 within the housings 24, 44. In this fashion, the surgeon can ensure that the proper disk height is attained prior to locking the rod members 16 to the pedicle screw assemblies 12, 14. This screw distraction may be accomplished using any number of suitable instruments. The locking screws 26, 46 may be secured or locked within the respective housing 24, 44 via any number of suitable mechanisms, including but not limited to the manner shown, namely threading the exterior of the locking screws 26, 46 and providing grooves along the interior of the housings 24, 44.

The spinal fixation system 10 of the present invention is suitable for both open and/or percutaneous procedures. In an open procedure, any or all of the components of the pedicle screw systems 12, 14 and rod member 16 may be introduced without the assistance of a K-wire (and, for that matter, such components may be non-cannulated). During a percutaneous procedure, however, both the pedicle screw assemblies 12, 14 and rod member 16 may be introduced percutaneously through the use of K-wire guidance. According to one embodiment, this may be accomplished by percutaneously (i.e. using a K-wire for guidance) introducing a first fixed pedicle screw assembly 12 into a first vertebral body, introducing a first poly-axial pedicle screw assembly 14 in an adjacent vertebral body, creating an incision extending between and down to the first fixed and poly-axial pedicle screw assemblies 12, 14, introducing the rod member 16 into the housings 24, 44, respectively, (optionally distracting), and introducing the locking screws 26, 46 to lock the rod member 16 relative to the pedicle screw assemblies 12, 14. In this fashion, the ball portion 34 of the rod member 16 will be locked in the housing 24 and the rod portion 36 will be locked in the housing 44. The K-wires 80 may then be withdrawn. Any number of suitable instruments may be employed to facilitate the above-identified steps, including but not limited to a screwdriver for screwing the locking screws 26, 46 into the housings 24, 44.

Figure 3:
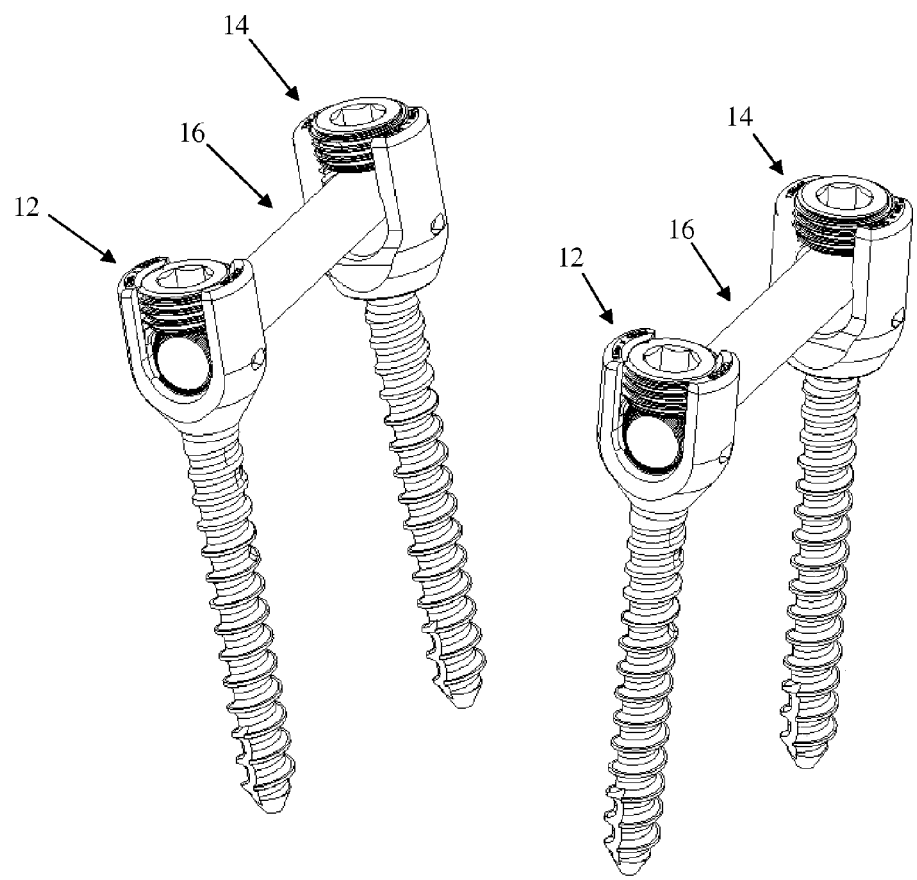
FIG. 3 is a perspective view of the spinal fixation system of the present (sans transverse connector) after implantation as shown in FIG. 2.
Figure 4:
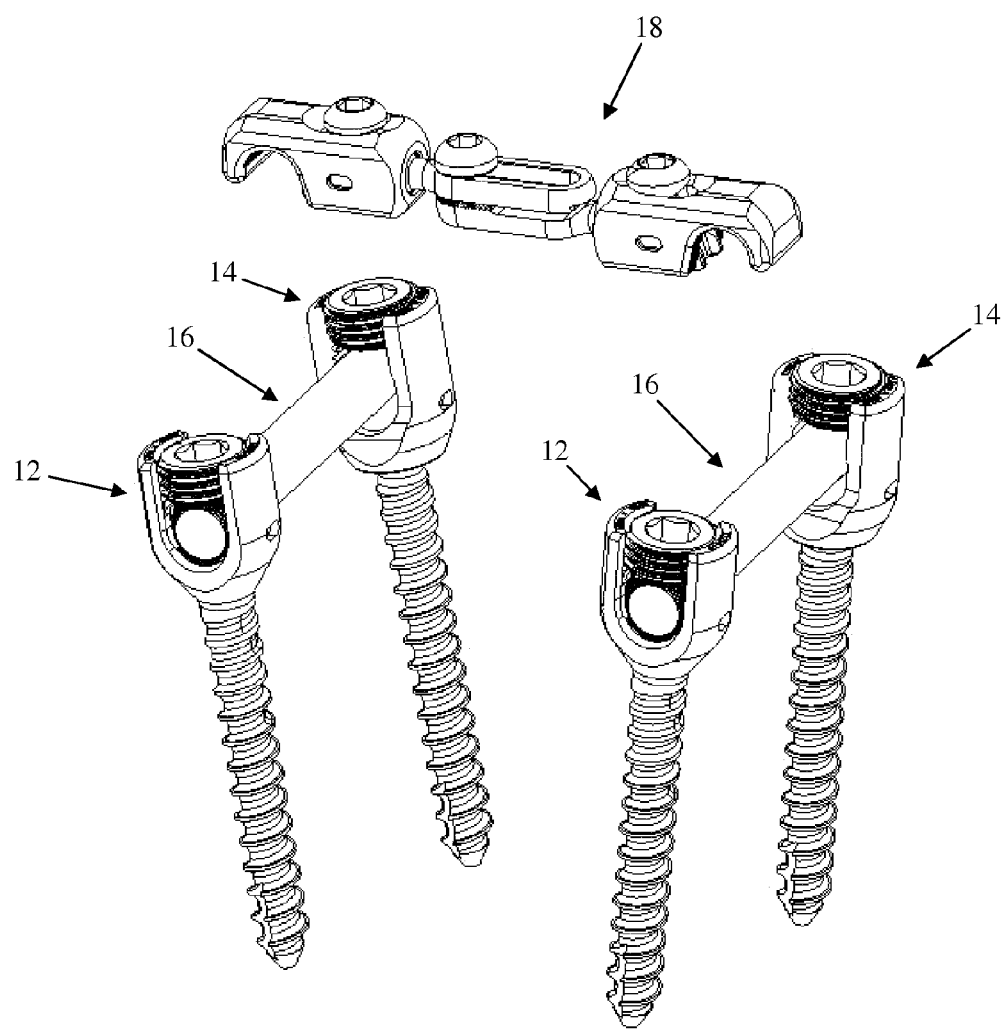
FIG. 4 is a perspective view of the transverse connector of the present invention being introduced onto the rod members of the spinal fixation system of the present invention.

In either event (open or percutaneous introduction), the spinal fixation system 10 of the present invention, once implanted, will appear as shown in FIG. 3. As shown in FIG. 4, the transverse connector 18 of the present invention may thereafter be employed to establish a rigid coupling between the adjacent rod members 16.

Figure 5:
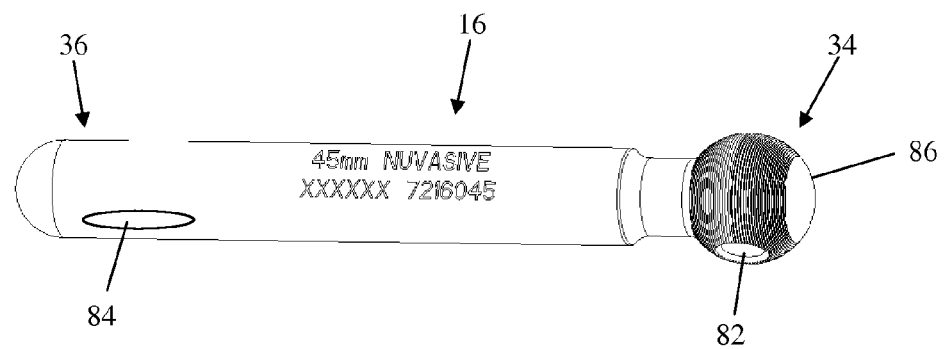
FIGS. 5-6 are side views of the rod member according to the present invention.
Figure 6:
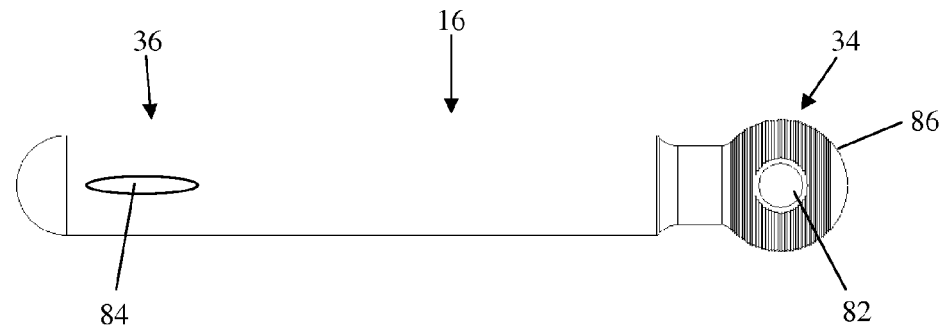

The rod member 16 will now be described in detail with reference to FIGS. 5-6. As set forth above, the rod member 16 of the present invention includes the ball portion 34 at one end and the rod portion 36 at the other end. According to the present invention, the ball portion 34 and/or the rod portion 36 may be cannulated for purposes of accommodating a K-wire for guiding the rod member 16 into the patient, such as represented by cannulations 82, 84. The cannulation 82 is preferably provided as a generally cylindrical lumen extending through the general center of the ball portion 34 such that it the center of the ball portion 34 may be guided directly into the spherical receiving area within the housing 24 (or housing 44 if the rod member 16 is reversed). The cannulation 84, on the other hand, has a generally elongated shape to accommodate variations in the distance between the housing 24 and housing 44, which may exist due to surgeon placement or other factors. According to the present invention, the ball portion 34 is equipped with a plurality of circumferential ridges 86 disposed generally perpendicularly to the longitudinal axis of the rod member 16. As will be described below, these circumferential ridges 86 cooperate with circumferential ridges provided within the housings 24, 44 such that, when the ball portion 34 is locked therein, the two areas of circumferential ridges engage and meld together to prevent any rotation or movement therebetween. The rod member 16 of the present invention may be of any length suitable or desirable to connect two or more vertebrae, and may be generally provided in a range of 25-300 mm.

Figure 7:
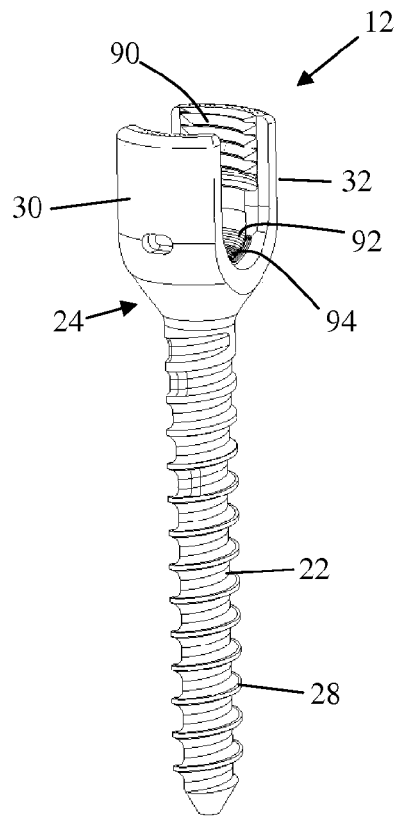
FIGS. 7-9 are perspective, side and top views, respectively, of a fixed angle pedicle screw assembly of the present invention, having a shaft diameter of 5.5 mm and a length of 45 mm.
Figure 8:
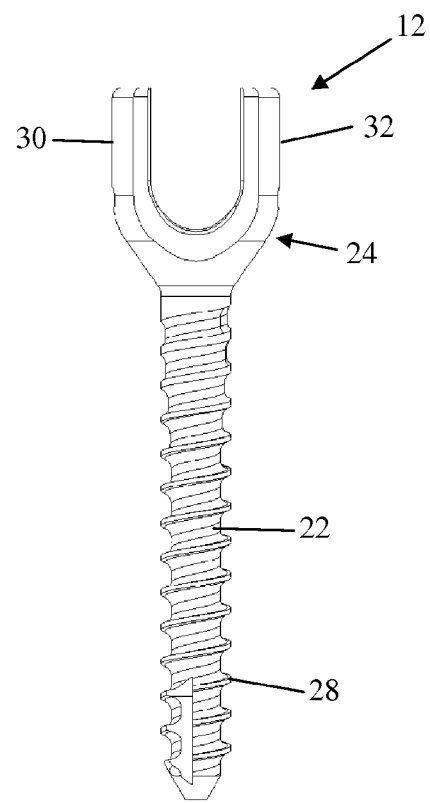
Figure 9:
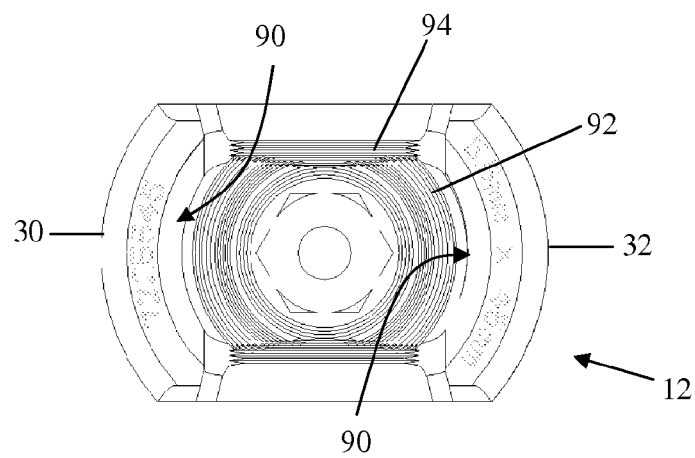

Various aspects of the fixed angle pedicle screw assembly 12 of the present invention will now be described in detail with reference to FIGS. 7-9. According to one embodiment of the present invention, the interior of the first and second branches 30, 32 are provided with grooves 90 to threadedly engage with threads provided on the exterior of the locking screw 26. The grooves 90 and threads on the locking screw 26 may be configured such that the first and second branches 30, 32 are pulled together to prevent splaying during introduction of the locking screw 26 or due to use, such as by establishing a helical point-contact between the grooves 90 and threads on the locking screw 26. In a still further aspect of the present invention, the bottom of the housing 24 is provided with a plurality of circumferential grooves 92 and 94 dimensioned to engage with the circumferential grooves 86 on the ball portion 34 of the rod member 16. As mentioned above, this bolsters the purchase between the ball portion 34 and housing 26 such that the two are more effectively locked in position relative to one another after the locking screw 26 has been tightened. FIG. 8 best illustrates the "U" shaped opening in the housing 24, which may accommodate either the ball portion 34 and/or rod portion 36 of a rod member 16.

According to a still further aspect of the present invention, the thread 28 is designed to have a uniform pitch regardless of the diameter of the shaft 22. For example, as shown in FIGS. 10-12, the thread 28 has the same pitch for the 6.5 mm diameter shaft 22 as in the 5.5 mm diameter shaft 22 shown in FIGS. 7-9. In similar fashion, as shown in FIGS. 13-15, the thread 28 has the same pitch for the 7.5 mm diameter shaft 22 as in the 5.5 mm diameter shaft 22 shown in FIGS. 7-9 and the 6.5 mm diameter shaft 22 shown in FIGS. 10-12. This is advantageous, among other reasons, because it provides the ability to use the same cutting tools for all sizes of the thread form. The fixed angle pedicle screw assembly of the present invention may be of any length and width suitable or desirable to purchase the vertebrae, and may be generally provided with a width range of 5.5-7.5 mm and a length range of 30-50 mm.

Figure 16:
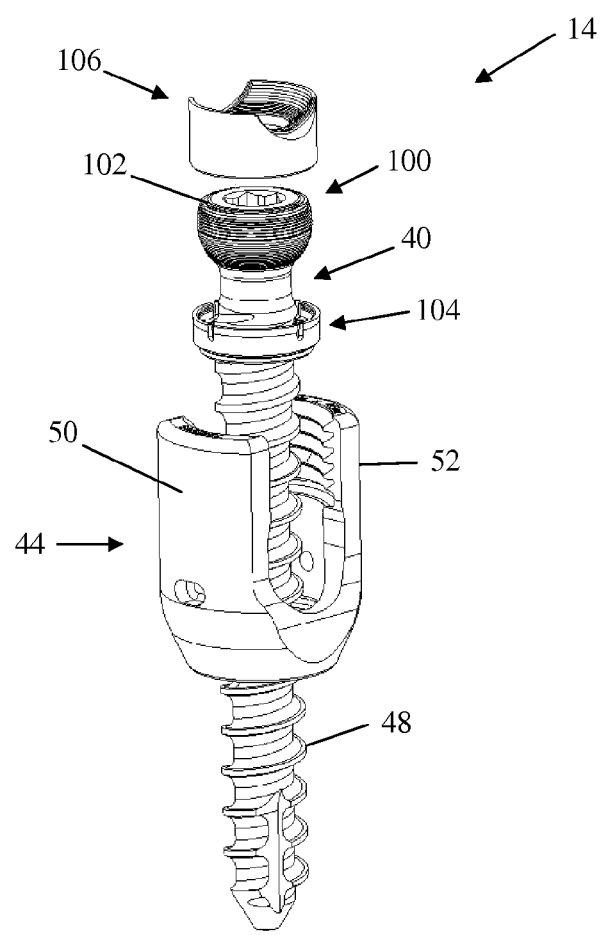
FIG. 16 is a perspective exploded view of a poly-axial pedicle screw assembly according to one embodiment of the present invention.
Figure 20:
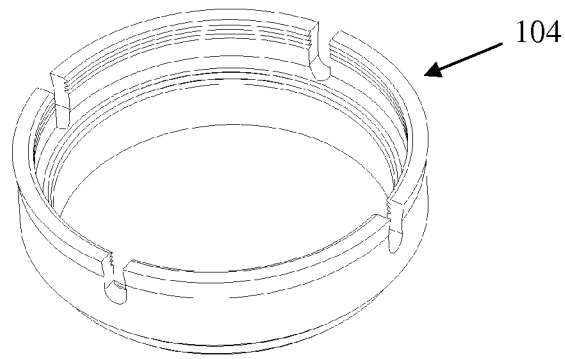
FIGS. 20-22 are perspective, side and top views, respectively, of a pivot ring forming part of the poly-axial pedicle screw system of the present invention.
Figure 21:
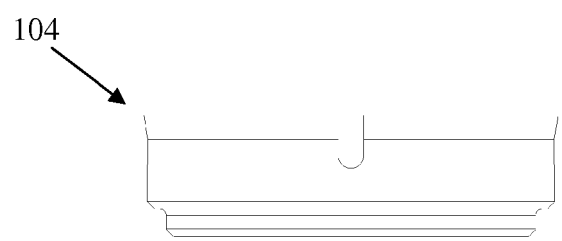
Figure 22:
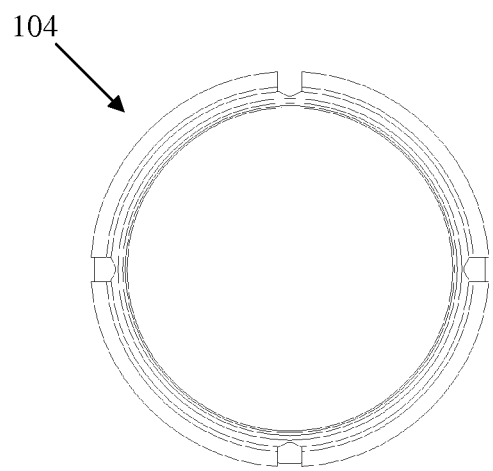

Various aspects of the poly-axial pedicle screw assembly 14 of the present invention will now be described in detail. As best shown in FIG. 16, the screw member 40 and a housing 44 are separate articles. With combined reference to FIGS. 16-19, the screw member 40 includes a hemi-spherical head region 100, which according to a preferred embodiment is equipped with a plurality of circumferential grooves 102. As best shown in FIG. 19, the screw member 40 is cannulated to receive a K-wire for guidance and includes a hex-type receiving area in the head region 100 to receive a screwdriver instrument. To facilitate the cooperation and engagement between the screw member 40 and the housing 44, the poly-axial pedicle screw assembly 14 is provided with a pivot ring 104 and a load ring 106. With combined reference to FIGS. 16 and 20-22, the pivot ring 104 is dimensioned to rest within a region within the bottom of the housing 44 and allow the head region 100 to pivot within the housing 44 prior to being locked in position. With combined reference to FIGS. 16 and 23-26, the load ring 106 will rest on top of the head portion 100 of the screw member 40 and forms the receiving area for the ball portion 34 and/or rod portion 36 of the rod member 16 of the present invention. To facilitate this, the load ring 106 is equipped with a plurality of circumferential grooves 108 and 110 to engage and lock with the circumferential grooves 86 provided on at least the ball portion 34. The poly-axial pedicle screw assembly of the present invention may be of any length and width suitable or desirable to purchase the vertebrae, and may be generally provided with a width range of 5.5-7.5 mm and a length range of 30-55 mm.

Figure 27:
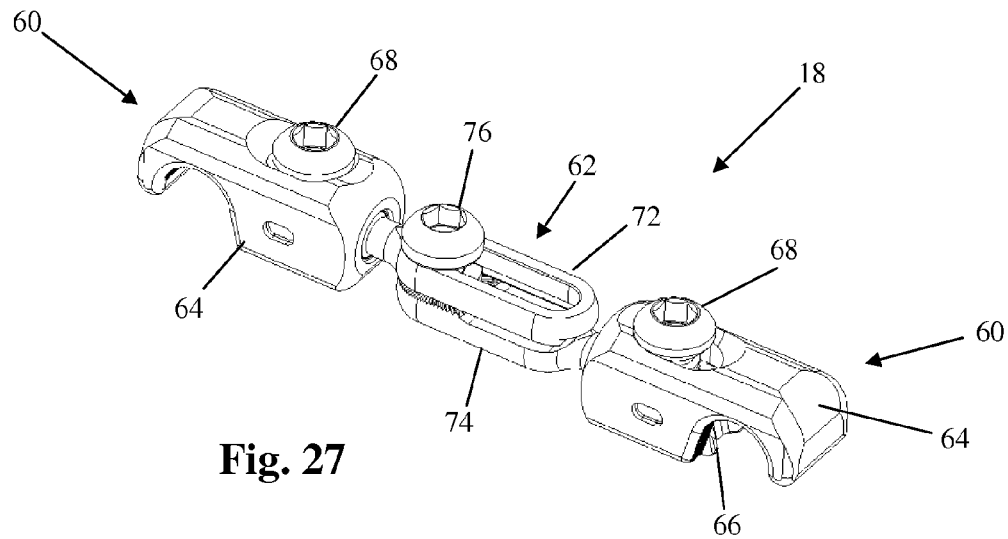
FIGS. 27-29 are perspective, side and top views, respectively, of an example of a transverse connector according to one embodiment of the present invention.
Figure 28:
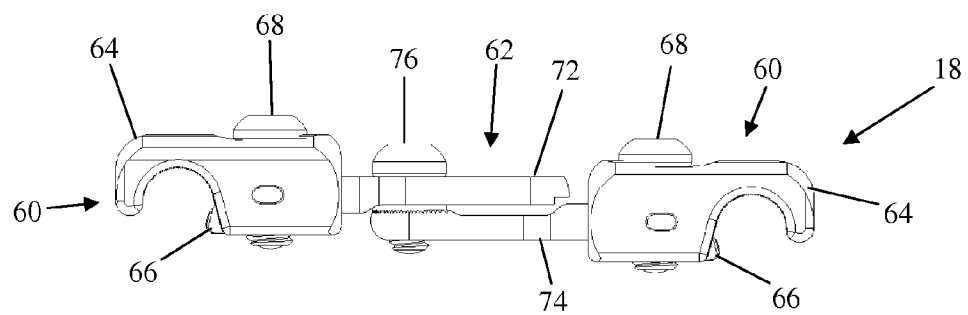
Figure 29:
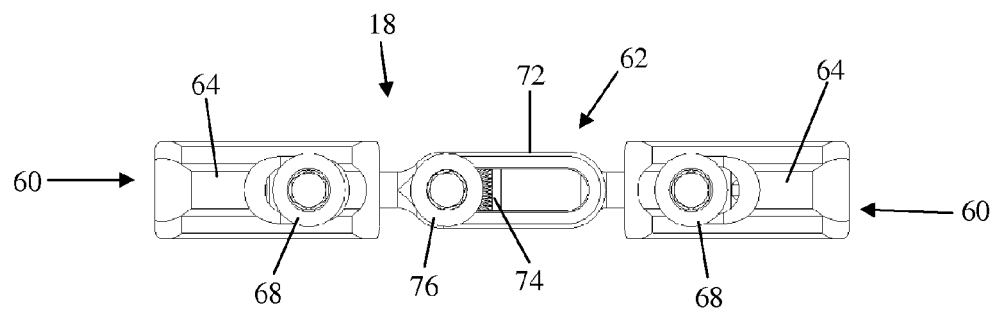
Figure 30:
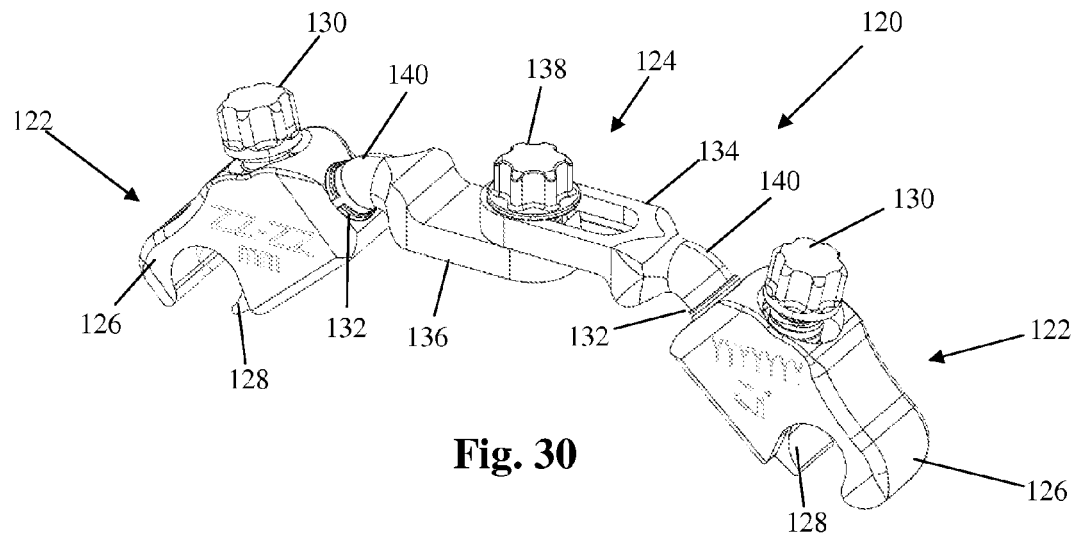
FIGS. 30-32 are perspective, side, and top views, respectively, of an example of a transverse connector according to an alternative embodiment of the present invention.
Figure 31:
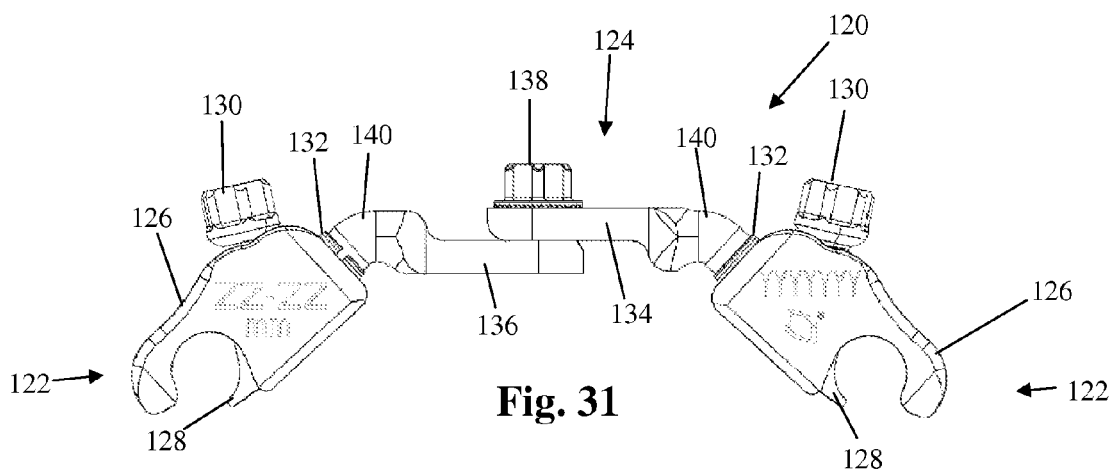
Figure 32:
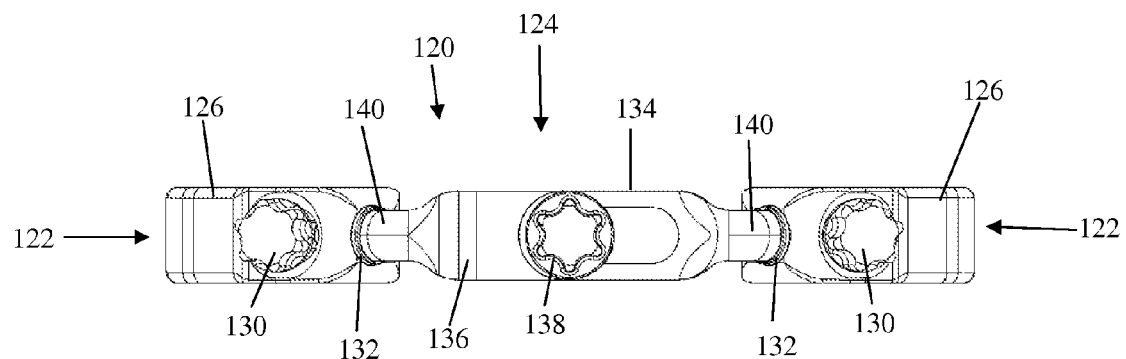
Figure 33:
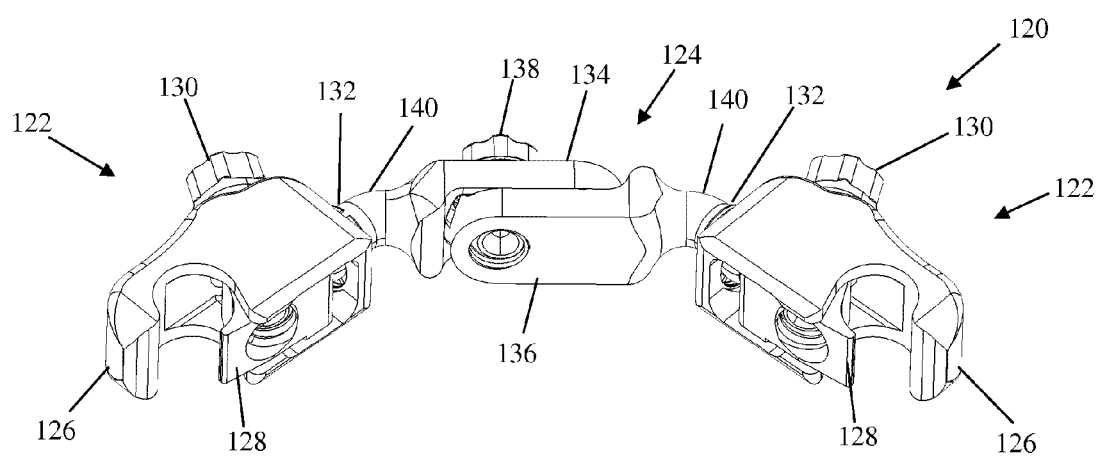
FIG. 33 is a bottom perspective view of the transverse connector of FIG. 30.
Figure 34:
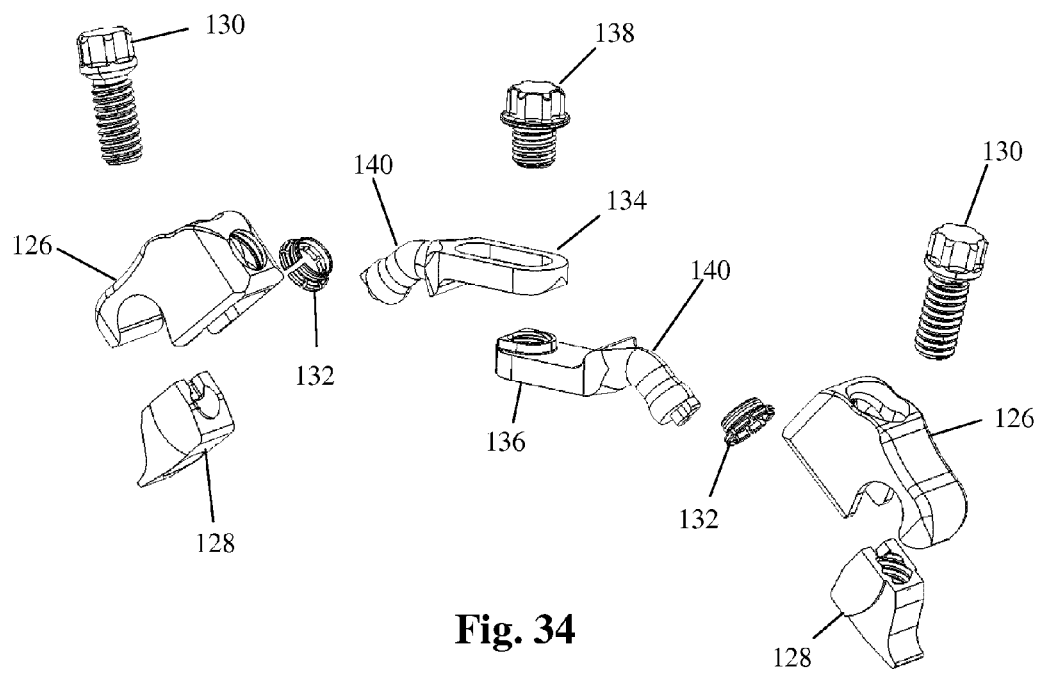
FIG. 34 is an exploded perspective view of the transverse connector of FIG. 30.
Figure 35:
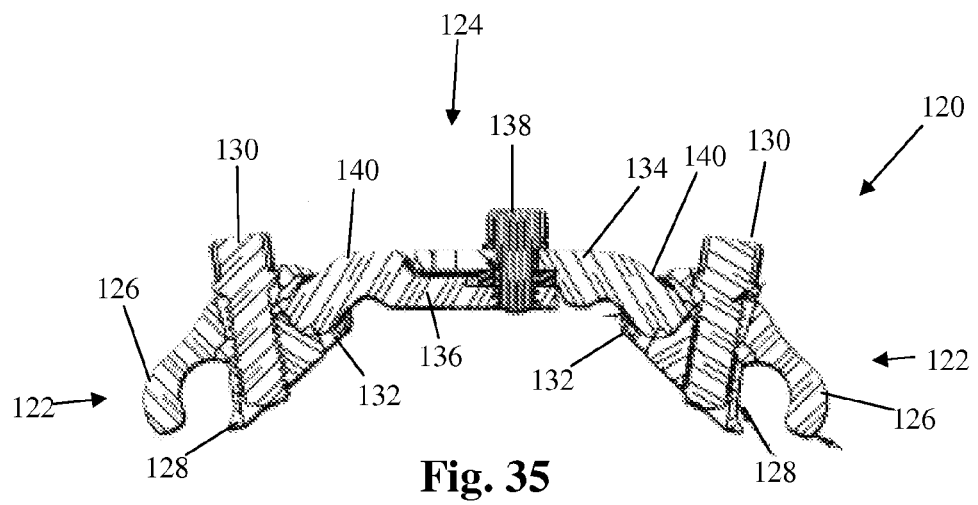
FIG. 35 is a side cross-sectional view of the transverse connector of FIG. 30.
Figure 36:
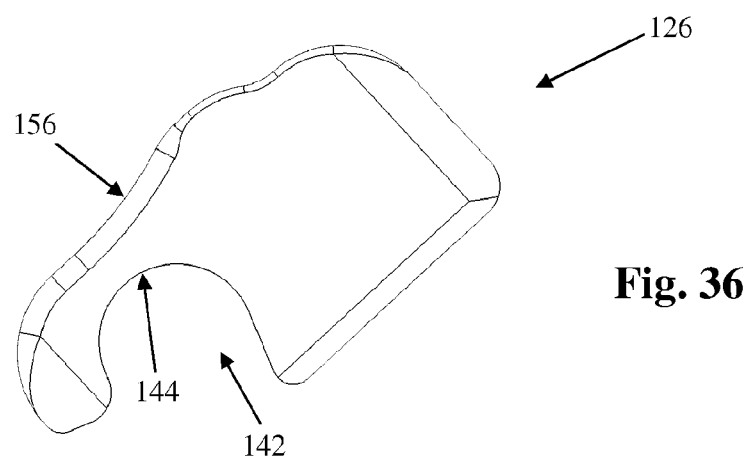
FIGS. 36-37 are side plan and bottom plan views, respectively, of an example of a first clamp member forming part of the transverse connector of FIG. 30.
Figure 37:
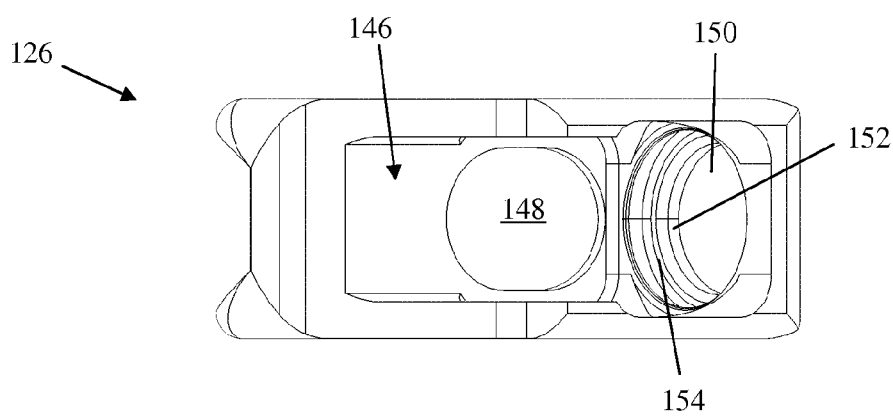
Figure 38:
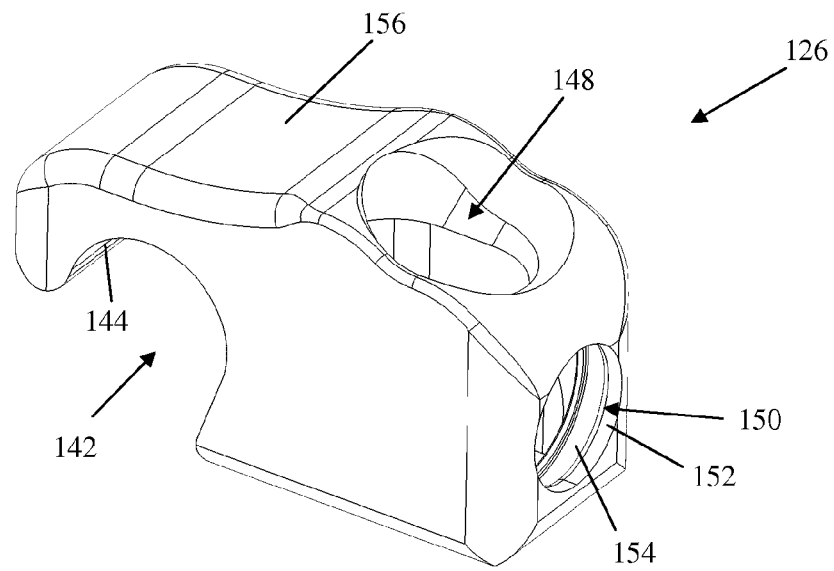
FIGS. 38-39 are top perspective and bottom perspective views, respectively, of the first clamp member of FIG. 36.
Figure 39:
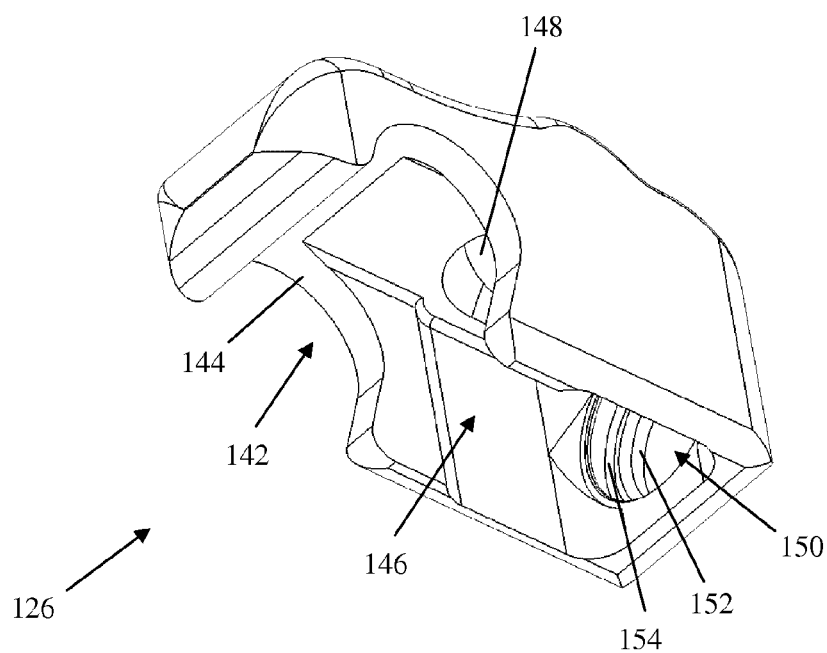

With reference to FIGS. 27-29, the transverse connector 18 of the present invention includes a pair of rod clamping assemblies 60 capable of fixedly engaging regions on the respective rod members 16, as well as a linkage assembly 62 extending between the rod clamping assemblies 60. Each rod clamping assembly 60 includes a top clamp member 64, a bottom clamp member 66 (not shown), a clamp screw 68, and a poly-axial pivot ring 70 (not shown). The linkage assembly 62 includes a slotted link member 72, a grooved link member 74, and a link screw 76. The transverse connector 18 of the present invention may be of any length suitable or desirable to stabilize a pair of rods, and may be generally provided with a length range of 45-100 mm.

With reference to FIGS. 30-35, an alternative transverse connector 120 of the present invention includes a pair of rod clamping assemblies 122 capable of fixedly engaging regions on the respective rod members 16, as well as a linkage assembly 124 extending between the rod clamping assemblies 122. Each rod clamping assembly 122 includes a first clamp member 126, a second clamp member 128, a clamp screw 130, and a poly-axial pivot ring 132. The linkage assembly 124 includes a first link member 134, a second link member 136, and a link screw 138. The transverse connector 120 of the present invention may be of any length suitable or desirable to stabilize a pair of rods, and may be generally provided with a length range of 45-100 mm. Transverse connector 120 differs from transverse connector 18 in that the rod clamping assemblies 122 are oriented at an angle offset from the longitudinal axis of the connector. This angle may be any angle between zero and ninety degrees without departing from the scope of the present invention. To accomplish this angle, transverse connector 120 includes nonlinear shaft portions 140 extending between the first link member 134 and rod clamping assembly 122 on one side of the transverse connector 120, and the second link member 136 and rod clamping assembly 122 on the other side of the transverse connector 120. Nonlinear portions 140 may be angled, curved, bent, or generally arcuate in shape without departing from the scope of the present invention.

The transverse connector 120 shown and described herein includes a pair of clamping assemblies 122. The clamping assemblies 122 are identical in features, differing only in that one clamping assembly 122 is coupled to the first link member 134, and the other clamping assembly 122 is coupled to the second link member 136. Therefore, each component part of the clamping assemblies 122 (e.g. first clamp member 126, second clamp member 128, clamp screw 130, and poly-axial pivot ring 132) are described herein below in the singular; however it will be understood that the transverse connector 120 as shown includes a pair of each component.

FIGS. 36-39 illustrate the first clamp member 126 in greater detail. The first clamp member 126 includes a recess 142 configured to receive a rod member 16 of the surgical fixation system 10 described above. The recess 142 includes a first arced engagement surface 144 having a semi-circular cross-section, dimensioned to engage with the rod member 16 upon use. The first clamp member 126 further includes a cavity 146 formed within the first clamp member 126 and in communication with the recess 142. As will be explained in further detail below, the cavity 146 is configured to receive the second clamp member 128 therein. The first clamp member 126 further includes a first aperture 148 dimensioned to receive the clamp screw 130 therethrough, and a second aperture 150 dimensioned to receive the poly-axial pivot ring 132 and the distal engagement member 188 of the first link member 134 (or conversely, the distal engagement member 204 of the second link member 136). The second aperture 150 includes a lip 152 and a recess 154 positioned underneath the lip 152. As will be explained below, the lip 152 and recess 154 cooperate to aid in securing the pivot ring 132 (and link member) to the first clamp member 126. The first clamp member 126 is provided with a generally smooth and contoured superior surface 154 in order to minimize trauma to the surrounding tissues post-implantation. Generally, any or all of the edges on the transverse connector 120 may be contoured or rounded to minimize tissue disruption.

Figure 40:
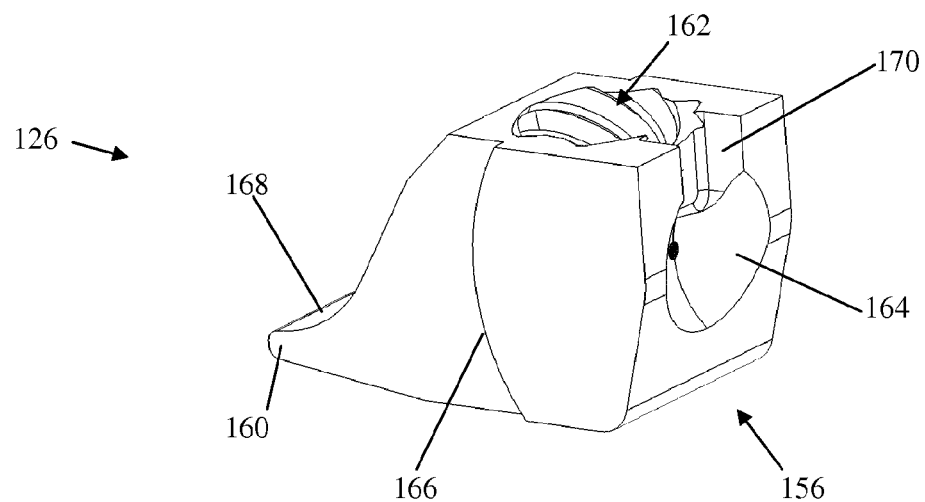
FIGS. 40-41 are perspective views of an example of a second clamp member forming part of the transverse connector of FIG. 30.
Figure 41:
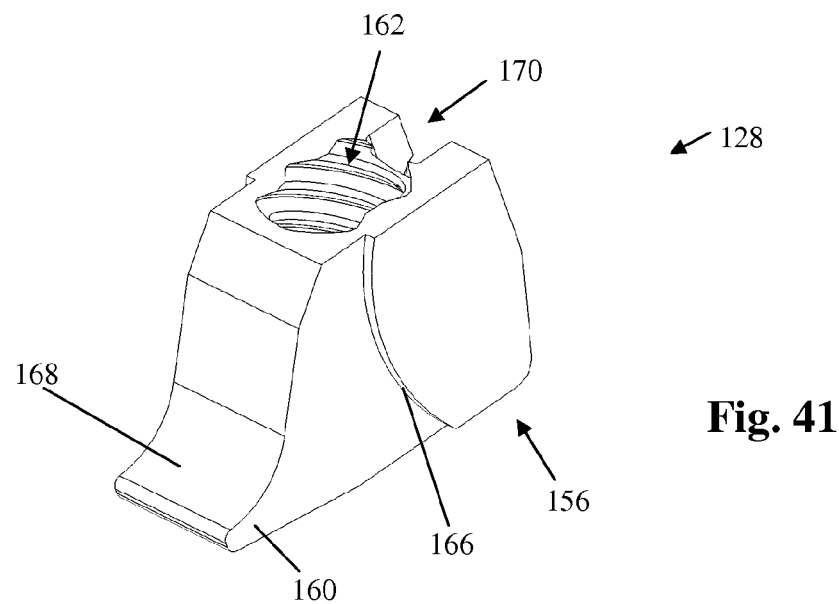
Figure 42:
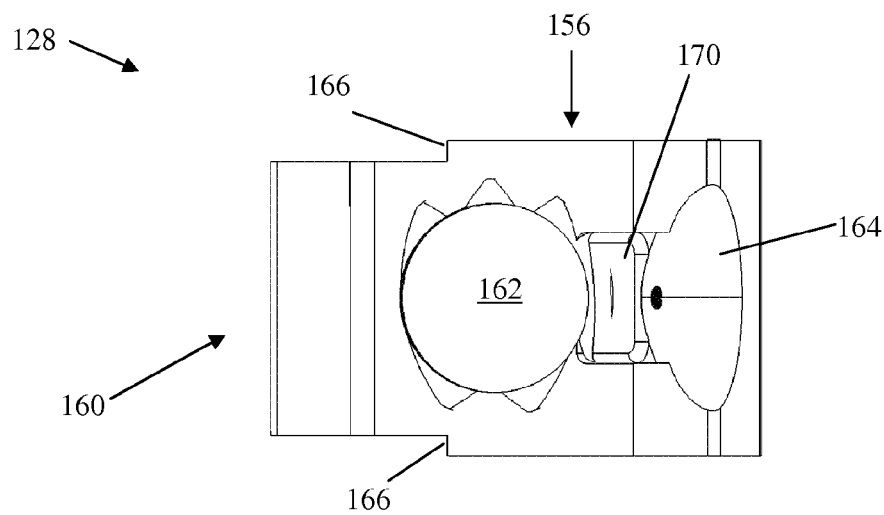
FIG. 42 is a top plan view of the second clamp member of FIG. 40.

FIGS. 40-42 illustrate the second clamp member 128 in greater detail. The second clamp member 128 includes a body portion 156 and a flange 158 extending from the body portion. The body portion further includes a screw aperture 160 extending therethrough and a first recess 164 for receiving the distal engagement member 188 of the first link member 134 (or conversely, the distal engagement member 204 of the second link member 136). A second recess 170 is provided just above the first recess 164. The second recess 170 cooperates with the knob structure 198 of the distal engagement member 188 of the first link member 134 (or conversely, the distal engagement member 204 of the second link member 136) in order to ensure proper orientation of the second clamp member 128 during implantation. The screw aperture 160 may be threaded in order to provide secure engagement with the clamp screw 130. The screw aperture 164 may be provided in a generally vertical orientation relative to the body portion 156, however in a preferred embodiment (shown by way of example only) the screw aperture 162 extends obliquely through the body portion 156. This is to facilitate an optimum angle for the user to insert the clamp screw 130 through the device in a minimally invasive operative corridor. The body portion 156 further includes a pair of lateral curved surfaces 166 dimensioned to engage the first clamp member 126 and facilitate pivoting of the second clamp member 128 if necessary to engage a rod 16. The flange 160 includes a second arced engagement surface 168 dimensioned to engage with the rod member 16 upon use.

Figure 43:
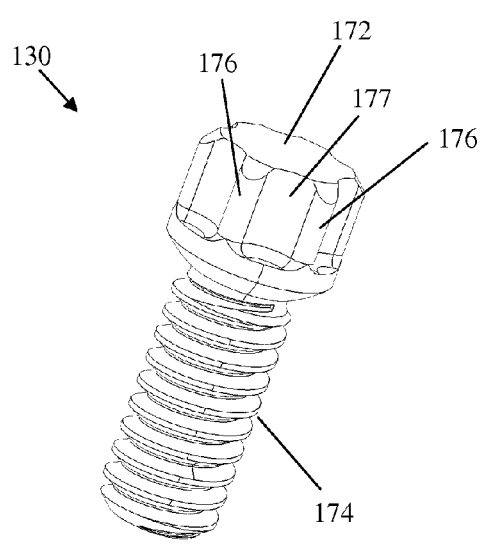
FIG. 43 is a perspective view of an example of a clamp screw forming part of the transverse connector of FIG. 30.

FIG. 43 illustrates an example of a clamp screw 130 according to one embodiment of the present invention. The clamp screw 130 includes a head 172 and elongated shaft 174 extending distally from the head 172. The head 172 includes a plurality of ridges 176 and/or recesses 177 to enable a user to grip the clamp screw 130 during insertion, using either a mechanical tool or several fingers. The elongated shaft 174 is threaded in order to engage with the threaded screw aperture of the second clamp member 128. The clamp screw 130 functions to secure the second clamp member 128 in position relative to the first clamp member 126 after implantation and securing to a spinal rod 16.

Figure 44:
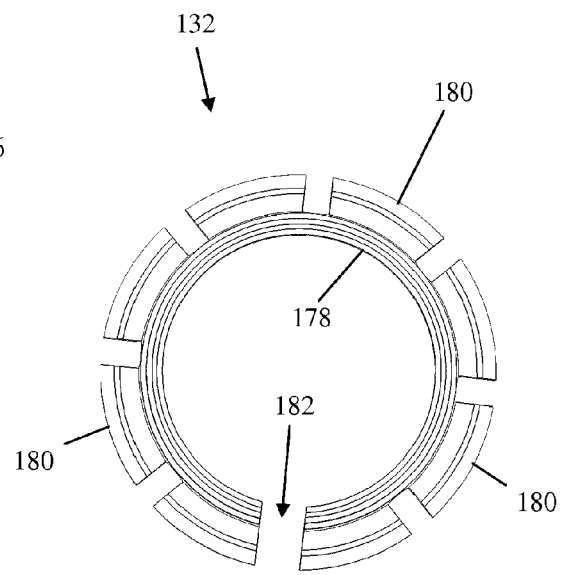
FIGS. 44-46 are top plan, top perspective, and bottom perspective views, respectively, of an example of a poly axial pivot ring of the transverse connector of FIG. 30.
Figure 45:
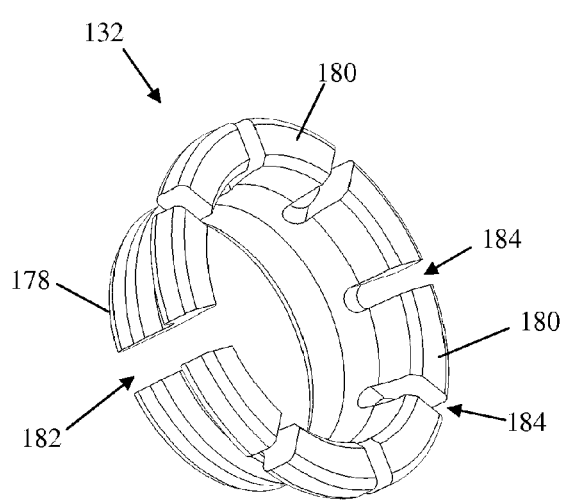
Figure 46:
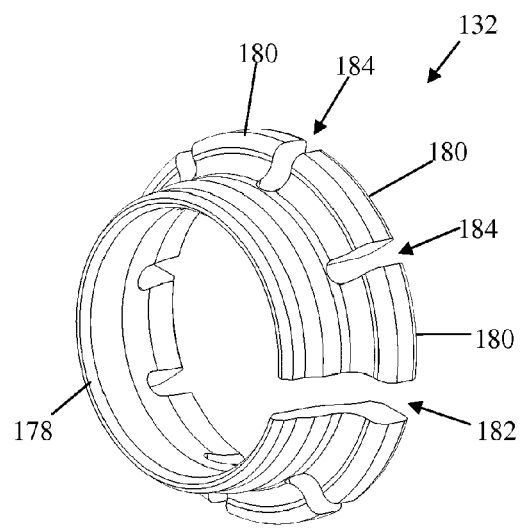
Figure 47:
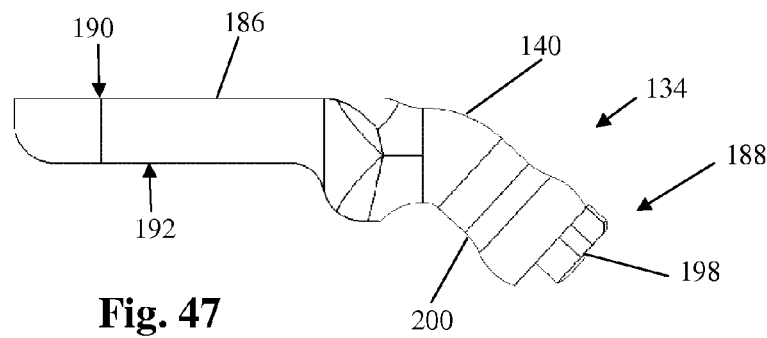
FIG. 47 is a plan view of an example of a first link member forming part of the transverse connector of FIG. 30.
Figure 48:
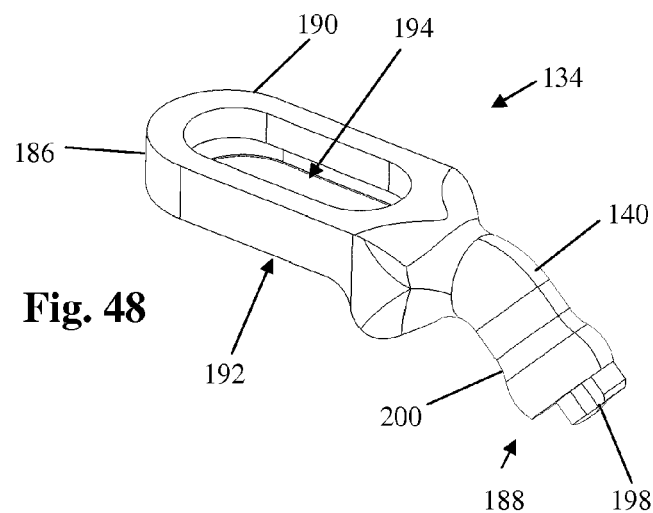
FIGS. 48-50 are perspective views of the first link member of FIG. 47.
Figure 49:
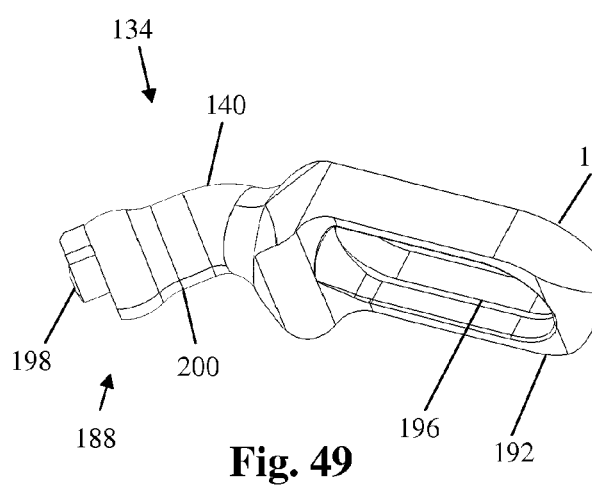
Figure 50:
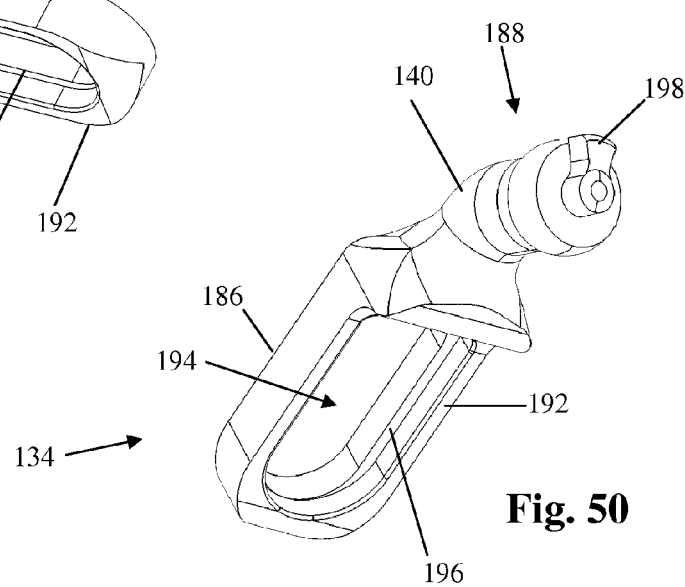

FIGS. 44-46 illustrate and example of a poly-axial pivot ring 132 according to one embodiment of the present invention. The poly-axial pivot ring 132 includes a base portion 178 and a plurality of flanges 180. The base portion 178 forms a near circle broken by a gap 182. The gap 182 allows slight compression of the pivot ring 132 in response to desired movement of the first clamp member 126 relative to the first or second link members 134, 136. The flanges 180 extend radially from the base portion 178 and are separated by cutouts 184. As with the gap 182, the cutouts 184 allow slight compression of the pivot ring 132, allowing controlled pivoting of the clamp assembly 122 during implantation. The flanges 180 are dimensioned to be received within the second recess 154 of the first clamp member 126, as illustrated by way of example in FIGS. 56-67. When fully assembled, the flanges 180 and the lip 152 prevent the first or second link member 134, 136 from disengaging from the first clamp member 126.

FIGS. 47-50 illustrate an example of a first link member 134 according to one embodiment of the present invention. The first link member 134 includes a body portion 186 and a distal engagement member 188, which are separated by a nonlinear shaft 140. The body portion 186 includes a generally planar top surface 190, a generally planar bottom surface 192, and an elongated slot 194 through the body portion 186 between the top and bottom surfaces 190, 192. The bottom surface further includes a recess 196 adjacent to and substantially surrounding the elongated slot 194. The recess 196 functions to engage with the raised platform 212 of the second link member 136 to ensure controlled linear translation of the first link member 134 relative to the second link member 136. Essentially, the recess 196 functions as a track (or groove) for the raised platform 212 of the second link member 136 to translate linearly along without becoming dislodged or otherwise flopping around in the surgical area. The distal engagement member 188 includes a knob structure 198 extending distally from the distal engagement member 188. The knob structure 198 is dimensioned to be received within the first and second recesses 164, 170 of the second clamp member 128 (shown in FIG. 56) to enable controlled movement of the second clamp member 128 during implantation. The nonlinear shaft 140 includes a recessed portion 200 dimensioned to receive the poly-axial pivot ring 132 thereon. The nonlinear shaft 140 is a significant aspect of the transverse connector 120 in that it allows for greater clearance of the transverse connector 120 relative to the bony structures after implantation.

Figure 51:
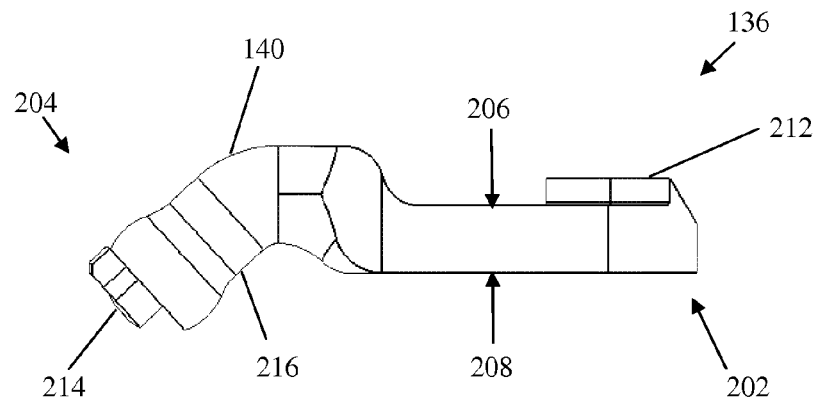
FIGS. 51-53 are plan, top perspective, and bottom perspective views, respectively, of an example of a second link member forming part of the transverse connector of FIG. 30.
Figure 52:
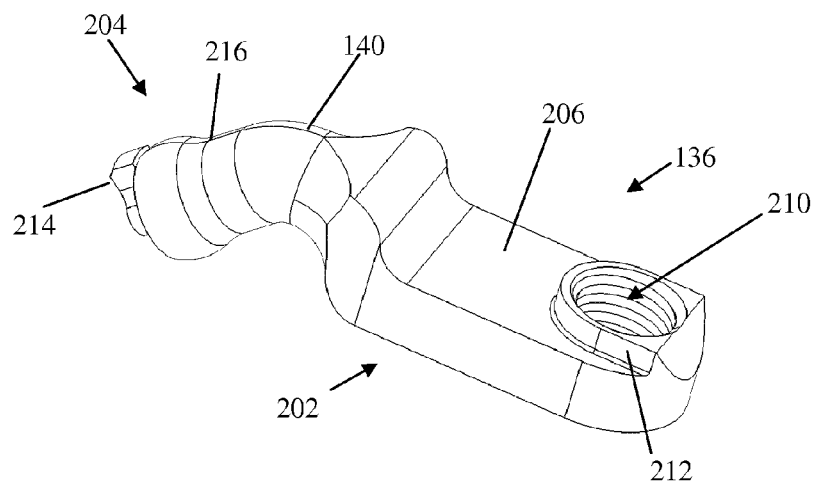
Figure 53:
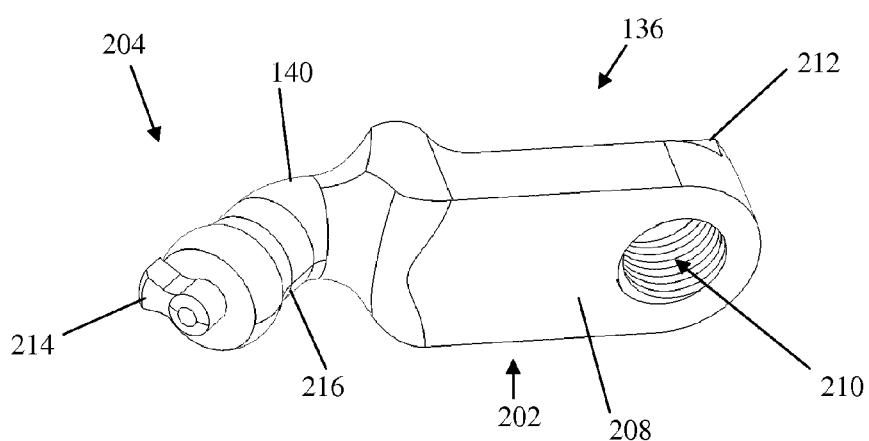

FIGS. 51-53 illustrate an example of a second link member 136 according to one embodiment of the present invention. The second link member 136 includes a body portion 202 and a distal engagement member 204, which are separated by a nonlinear shaft 140. The body portion includes a generally planar top surface 206, a generally planar bottom surface 208, and a screw aperture 210 extending through the body portion 202 between the top and bottom surfaces 206, 208. The screw aperture 210 is threaded and dimensioned to receive the link screw 138 therethrough. The top surface 206 further includes a raised platform 212 adjacent to and surrounding the screw aperture 210. As noted above, the raised platform 212 functions to engage with the recess 196 of the first link member 134 to ensure controlled linear translation of the first link member 134 relative to the second link member 136. The distal engagement member 204 includes a knob structure 214 extending distally from the distal engagement member 204. The knob structure 214 is dimensioned to be received within the first and second recesses 164, 170 of the second clamp member 128 (shown in FIG. 57) to enable controlled movement of the second clamp member 128 during implantation. The nonlinear shaft 140 includes a recessed portion 216 dimensioned to receive the poly-axial pivot ring 132 thereon. The nonlinear shaft 140 is a significant aspect of the transverse connector 120 in that it allows for greater clearance of the transverse connector 120 relative to the bony structures after implantation.

Figure 54:
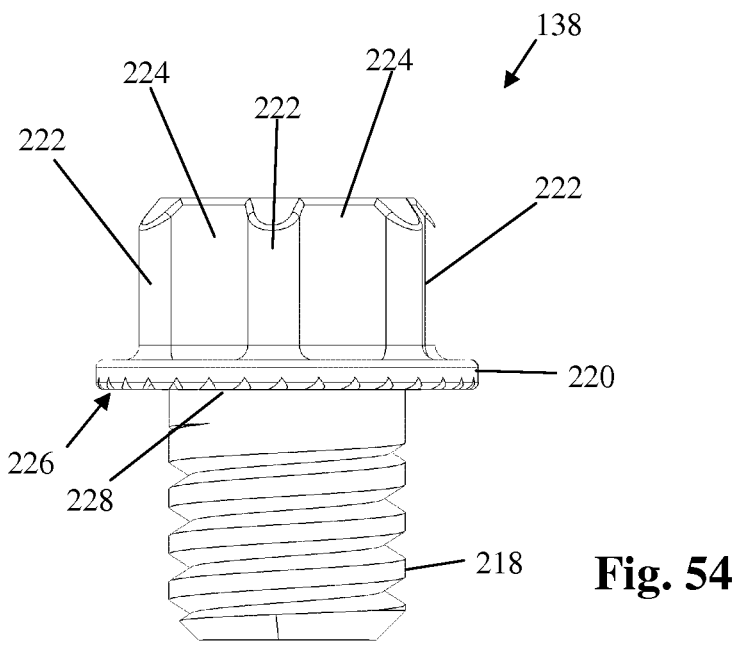
FIGS. 54-55 are plan and perspective views, respectively, of an example of a link screw forming part of the transverse connector of FIG. 30.
Figure 55:
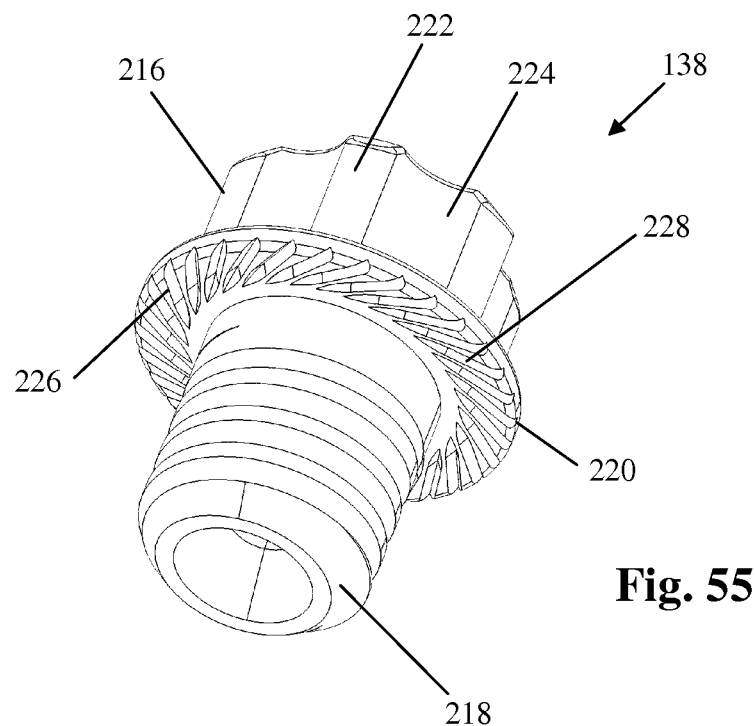

FIGS. 54-55 illustrate an example of a link screw 138 according to one embodiment of the present invention. By way of example only, the link screw 138 includes a head 216, a shaft 218, and a rim 220 positioned at the base of the head at the junction between the head 216 and shaft 218. The head 216 includes a plurality of ridges 222 and recesses 224 disposed between the ridges 222. The ridges 222 and/or recesses 224 function to enable a user to grip the link screw 138 during insertion, using either a mechanical tool or several fingers. The elongated shaft 218 is threaded to cooperate with the threaded aperture 210 of the second link member 136. The rim 220 has a diameter larger than the diameter of the head 216, and is dimensioned to extend over the top surface 190 of the first link member 134 upon assembly and implantation of the transverse connector 120. The rim 220 includes a generally planar bottom surface 226 facing away from the head 216 and configured to engage the top surface 190 of the first link member 134. The bottom surface 226 may include a surface roughening 228 along all or part of the bottom surface 226. The surface roughening 228 functions to provide frictional force relative to or purchase within the top surface 190 of the first link member 134 upon final tightening of the link screw 138 after implantation within a surgical target site. This will prevent the first and second link members 134, 136 from migrating relative to one another after implantation, ensuring that the transverse connector 120 is securely installed. The surface roughening 228 may be in any form capable of providing the intended result, including but not limited to (and by way of example only) ridges, grooves, protrusions (of any geometric shape), and the like.

Figure 56:
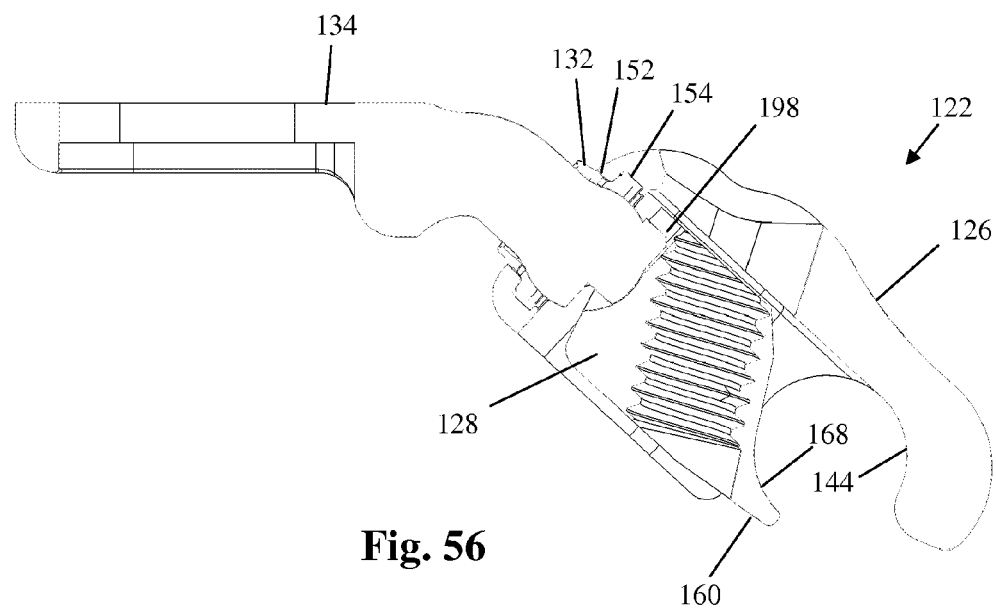
FIG. 56 is a cross-sectional view of an example of a linkage assembly engaged with a first link member forming part of the transverse connector of FIG. 30.
Figure 57:
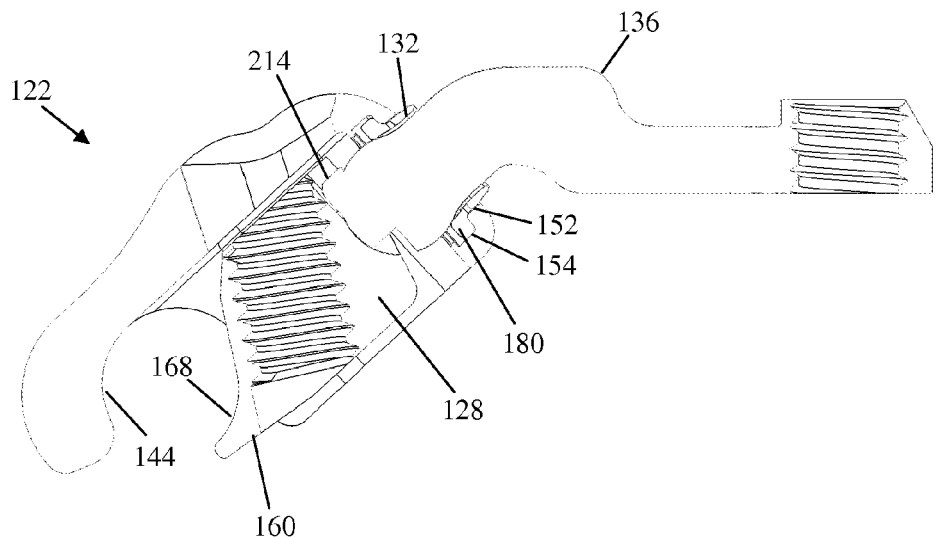
FIG. 57 is a cross-sectional view of an example of a linkage assembly engaged with a first link member forming part of the transverse connector of FIG. 30.

FIG. 56 is a cross-sectional view of a rod clamping assembly 122 coupled to a first link member 134. Of particular significance is the interaction between the pivot ring 132 and the lip member 152 and recess 154 of the first clamp member 126, as well as the interaction between the knob structure 198 of the first link member 134 and the second clamp member 128. FIG. 57 is a cross-sectional view of a rod clamping assembly 122 coupled to a second link member 136. Of particular significance is the interaction between the pivot ring 132 and the lip member 152 and recess 154 of the first clamp member 126, as well as the interaction between the knob structure 214 of the second link member 136 and the second clamp member 128.

In use, once the spinal fixation system 10 is implanted as described above, the transverse connector 120 may be employed to give stability to the construct. Initially, the transverse connector 120 is provided in a loosely assembled state, meaning that all of the parts are in their proper position, except for the clamp screws 130 and link screw 138. The clamp screws 130 and link screw 138 are in threaded engagement with the respective apertures, however only loosely. The clamping assemblies 122 are positioned on each rod member 16 such that the rod member 16 is positioned within the recess 142 of the first clamp member 126. The clamp screw 130 may then be threadedly advanced to tighten the screw within the screw aperture 160 of the second clamp member 128. As this occurs, the arced engagement surface 168 of the second clamp member 128 comes into contact with the rod member 16, also forcing the rod 16 into contact with the arced engagement surface 144 of the first clamp member 126. The flange 160 securely holds rod member 16 within the recess 142. This process is repeated for the other clamping assembly 122 on a second rod member 16. During this process, the overall length of the transverse connector 120 is adjustable due to linear translation capabilities of the first and second link members 134, 136. Once the construct has been successfully installed, final tightening occurs by tightening the link screw 138.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention.

What is claimed is:

1. A transverse connector that connects bilateral fixation rods of a spinal fixation system, a first of the bilateral fixations rods being fixed to at least first and second fixation anchors of the spinal fixation system and a second of the bilateral fixation rods being fixed to at least third and fourth fixation anchors of the spinal fixation system, comprising:

a linkage assembly including a first link and a second link coupled to the first link, a first clamping member coupled to the first link and having a free end configured to couple to said first fixation rod, and a second clamping member coupled to the second link and having a free end configured to couple to said second fixation rod, said first link being translatable relative to said second link along a first longitudinal axis of the linkage assembly, the first link including a first extension that extends obliquely to the first longitudinal axis and the second link including a second extension that extends obliquely from the first longitudinal axis, wherein the first clamping member is coupled to the first extension such that a second longitudinal axis of the first clamping member is oblique to the first longitudinal axis and wherein the second clamping member is coupled to the second extension such that a third longitudinal axis of the second clamping member is oblique to the first longitudinal axis, the first clamping member being coupled to the first extension via a joint such that the angle of the second longitudinal axis is adjustable relative to the first longitudinal axis and the second clamping member being coupled to the first extension via a second joint such that the angle of the third longitudinal axis is adjustable relative to the first longitudinal axis.

2. The transverse connector of claim 1, wherein said first link includes a first body portion having a first generally planar surface and a second generally planar surface opposite said first generally planar surface.

3. The transverse connector of claim 2, wherein said first body portion further includes an elongated slot formed through said body portion between said first and second generally planar surfaces.

4. The transverse connector of claim 3, wherein said second generally planar surface includes a recess substantially surrounding said elongated slot.

5. The transverse connector of claim 4, wherein said second link includes a second body portion having a third generally planar surface and a fourth generally planar surface opposite said third generally planar surface.

6. The transverse connector of claim 5, wherein said second body portion further includes a threaded aperture extending therethrough.

7. The transverse connector of claim 6, wherein said third generally planar surface includes a raised platform surrounding said threaded aperture.

8. The transverse connector of claim 7, wherein said raised platform is dimensioned to be snugly received within said recess.

9. The transverse connector of claim 7, wherein said raised platform has linear sides that are parallel to said first axis.

10. The transverse connector of claim 6, wherein said transverse connector further includes a link screw configured to threadedly engage said threaded aperture.

11. The transverse connector of claim 10, wherein said link screw includes head portion, a threaded shaft, and a rim positioned at the base of the head portion adjacent to the threaded shaft, the rim portion including a generally planar rim surface facing in the direction of the threaded shaft, the generally planar rim surface having surface roughening.

12. The transverse connector of claim 10, wherein tightening the link screw prevents translation between the first link and the second link.

13. The transverse connector of claim 1, wherein an end of the first extension includes a partially spherical surface.

14. The transverse connector of claim 13, wherein the first clamping member includes a first ring that mates with the partially spherical surface.

15. The transverse connector of claim 14, wherein the first clamping member includes a clamp screw that tightens the clamping member to the first fixation rod.

16. The transverse connector of claim 15, wherein tightening the clamp screw also prevents further adjustment of second longitudinal axis of the first clamping screw relative to the first longitudinal axis of the linkage assembly.

17. A method of connecting first and second bilaterally positioned spinal fixation rods coupled to at least two vertebrae in a spine, comprising the steps of:
coupling a transverse connector to said first and second fixation rods such that a first clamping element of the transverse connector is coupled to said first fixation rod and a second clamping element of the transverse connector is coupled to said second fixation rod, the first and second clamping elements being connected by a linkage assembly extending along a first axis and including a first link and a second link translatable relative to each other along the first longitudinal axis, wherein the first clamping member is coupled to an oblique extension of the link member via a joint such that the angle of a second longitudinal axis of the first clamping member is adjustable relative to the first longitudinal axis and the second clamping member is coupled to an oblique extension of the second link via a joint such that the angle of a third longitudinal axis of the second clamping member is adjustable relative to the first longitudinal axis.

* * * * *